(12) United States Patent
Cho et al.

(10) Patent No.: US 7,206,635 B2
(45) Date of Patent: Apr. 17, 2007

(54) METHOD AND APPARATUS FOR MODIFYING DELIVERY OF A THERAPY IN RESPONSE TO ONSET OF SLEEP

(75) Inventors: Yong Kyun Cho, Maple Grove, MN (US); Donald N. Jensen, Derwood, MD (US); Luc R. Mongeon, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 406 days.

(21) Appl. No.: 10/736,370

(22) Filed: Dec. 15, 2003

(65) Prior Publication Data

US 2004/0176809 A1 Sep. 9, 2004

Related U.S. Application Data

(63) Continuation-in-part of application No. 09/876,528, filed on Jun. 7, 2001, now Pat. No. 6,731,984.

(51) Int. Cl.
*A61F 1/365* (2006.01)

(52) U.S. Cl. ...................................................... 607/17

(58) Field of Classification Search ................ 600/373, 600/374, 377, 509, 513; 607/4–7, 9, 11, 607/17–20, 27, 116, 119, 122, 123
See application file for complete search history.

(56) References Cited

U.S. PATENT DOCUMENTS

| | | | |
|---|---|---|---|
| 3,941,135 A | 3/1976 | von Strum et al. | |
| 4,702,253 A * | 10/1987 | Nappholz et al. | 607/20 |
| 4,711,245 A | 12/1987 | Higgins et al. | |
| 4,795,542 A | 1/1989 | Ross et al. | |
| 5,101,831 A * | 4/1992 | Koyama et al. | 600/500 |
| 5,476,483 A * | 12/1995 | Bornzin et al. | 607/17 |
| 5,562,711 A | 10/1996 | Yerich et al. | |
| 5,630,834 A * | 5/1997 | Bardy | 607/5 |
| 5,733,312 A | 3/1998 | Schloss et al. | |
| 5,814,087 A | 9/1998 | Renirie | |
| 5,891,176 A | 4/1999 | Bornzin | |
| 5,964,788 A | 10/1999 | Greenhut | |
| 6,049,735 A | 4/2000 | Hartley et al. | |
| 6,055,454 A | 4/2000 | Heemels | |
| 6,122,536 A | 9/2000 | Sun et al. | |
| 6,128,534 A | 10/2000 | Park et al. | |
| 6,188,927 B1 | 2/2001 | Lu et al. | 607/17 |
| 6,775,571 B1 | 8/2004 | Kroll | 607/9 |
| 6,970,743 B2 * | 11/2005 | Weinberg et al. | 607/25 |
| 2002/0193839 A1 | 12/2002 | Cho et al. | 607/17 |
| 2003/0163059 A1 | 8/2003 | Poezevera et al. | 600/534 |
| 2005/0085734 A1* | 4/2005 | Tehrani | 600/484 |

FOREIGN PATENT DOCUMENTS

EP 1 060 761 A1 12/2000

* cited by examiner

*Primary Examiner*—Robert E. Pezzuto
*Assistant Examiner*—Frances P. Oropeza
(74) *Attorney, Agent, or Firm*—Michael C. Soldner; Girma Wolde-Michael

(57) ABSTRACT

A method and apparatus for providing a therapy to the patient that includes a therapy component configured to provide the therapy to the patient, sensing circuitry sensing a parameter of the patient, and a microprocessor coupled to the therapy component and the sensing circuitry to determine onset of a first state of the patient in response to the sensed physiologic parameter, and to determine whether the onset of the first state is detected for a predetermined time period.

39 Claims, 16 Drawing Sheets

METHOD AND APPARATUS FOR MODIFYING DELIVERY OF A THERAPY IN RESPONSE TO ONSET OF SLEEP

RELATED APPLICATION

This application is a continuation-in-part of application Ser. No. 09/876,528, filed Jun. 7, 2001, now U.S. Pat. No. 6,731,984 incorporated herein by reference in its entirety.

FIELD OF THE INVENTION

This invention relates generally to medical devices, and, more particularly to implantable medical devices for providing various types of therapies to patients.

BACKGROUND OF THE INVENTION

Implantable cardioverter defibrillators (ICDs) are capable of detecting cardiac arrhythmias and delivering electrical stimulation therapies to terminate arrhythmias. Tachycardia may be terminated by anti-tachycardia pacing therapies or high-voltage cardioversion shocks. Fibrillation may be terminated by high-voltage defibrillation shocks. These high-voltage shocks, which are referred to inclusively herein as "cardioversion/defibrillation shocks," can be life-saving to a patient but can be very painful.

Atrial arrhythmias, such as atrial tachycardia (AT) and atrial fibrillation (AF), may not be directly life-threatening and may occur repeatedly in some patients. Therefore, in order to avoid delivering frequent, painful shock therapies, atrial cardioversion/defibrillation therapies employing high-voltage shocks may be programmed to be disabled in an ICD, or programmed to be delivered after the AT/AF episode has been detected for a sustained period of time, for example 2 hours or longer. Atrial arrhythmia detection algorithms may remain enabled because a physician may want to monitor for the presence of AT and AF for the purposes of managing medical therapies, such as anti-coagulation therapy and anti-arrhythmic drugs. Furthermore, non-painful, anti-tachycardia pacing therapies may be delivered in an attempt to terminate a detected atrial arrhythmia. If these less aggressive therapies fail, however, or if all atrial arrhythmia therapies are disabled, the atrial arrhythmia may be sustained for long periods of time.

During sustained AT/AF episodes, blood stasis in the atria can result in the formation of clots or thrombus. If AT/AF is suddenly terminated, either spontaneously or through medical intervention, coordinated atrial contraction may dislodge the clot, producing thromboembolism and leading to a high risk of stroke. Furthermore, retrospective analysis of arrhythmia incidence in patients implanted with the Medtronic Model 7250 dual chamber ICD revealed that atrial fibrillation (AF) is a co-existent arrhythmia with ventricular tachycardia (VT) or ventricular fibrillation (VF) in a significant patient population. Approximately 18% of all VF episodes and 3% of all VT episodes were accompanied by recent onset AF or AT. Stein KM et al., J Am Coll Cardiol Proc., 1999. The termination of AT/AF using treatment modalities that are acceptable and tolerable to the patient is therefore desirable over sustained periods of untreated AT/AF. Atrial arrhythmia treatments that are tolerable to the patient are needed in order to increase patient acceptance and physician use of such therapies.

In U.S. Pat. No. 5,630,834, issued to Bardy, an automatic atrial defibrillator having the ability to determine whether the patient is likely to be asleep senses the occurrence of atrial fibrillation and delivers defibrillation pulses in response thereto. Defibrillation pulses which are at energy levels which would normally be painful to the patient are delivered only in response to occurrences of atrial fibrillation while the patient is determined to be asleep. Defibrillation pulses at lower, non-painful levels may be delivered while the patient is determined not to be asleep. Detection of the fact that the patient is sleeping can be accomplished using a real time clock, which may be used in conjunction with a physical activity sensor, and/or a posture sensor. A timekeeping method for sleep detection, however, is limited when the patient changes his/her bed time and/or wake time, travels to a different time zone, etc.

Detection of sleep based on time of day, even when combined with activity and/or posture, may not discriminate night time inactivity from a period of deep sleep, when a patient's perception of a normally painful defibrillation shock is most likely to be suppressed. In currently available ICD's, atrial defibrillation shocks may be scheduled to occur in the middle of the night, e.g., 2:00 A.M., in a patient having persistent AF. The patient may be aware that a defibrillation shock is scheduled to occur at a particular time during the night and, in anticipation of the impending shock, remain awake.

A need remains, therefore, for a method and apparatus for delivering therapies that are uncomfortable or painful to a patient during a period of deep sleep such that the discomfort perceived by the patient is suppressed.

BRIEF DESCRIPTION OF THE DRAWINGS

The invention may be understood by reference to the following description taken in conjunction with the accompanying drawings, in which like reference numerals identify similar elements, and in which.

Figure 1:
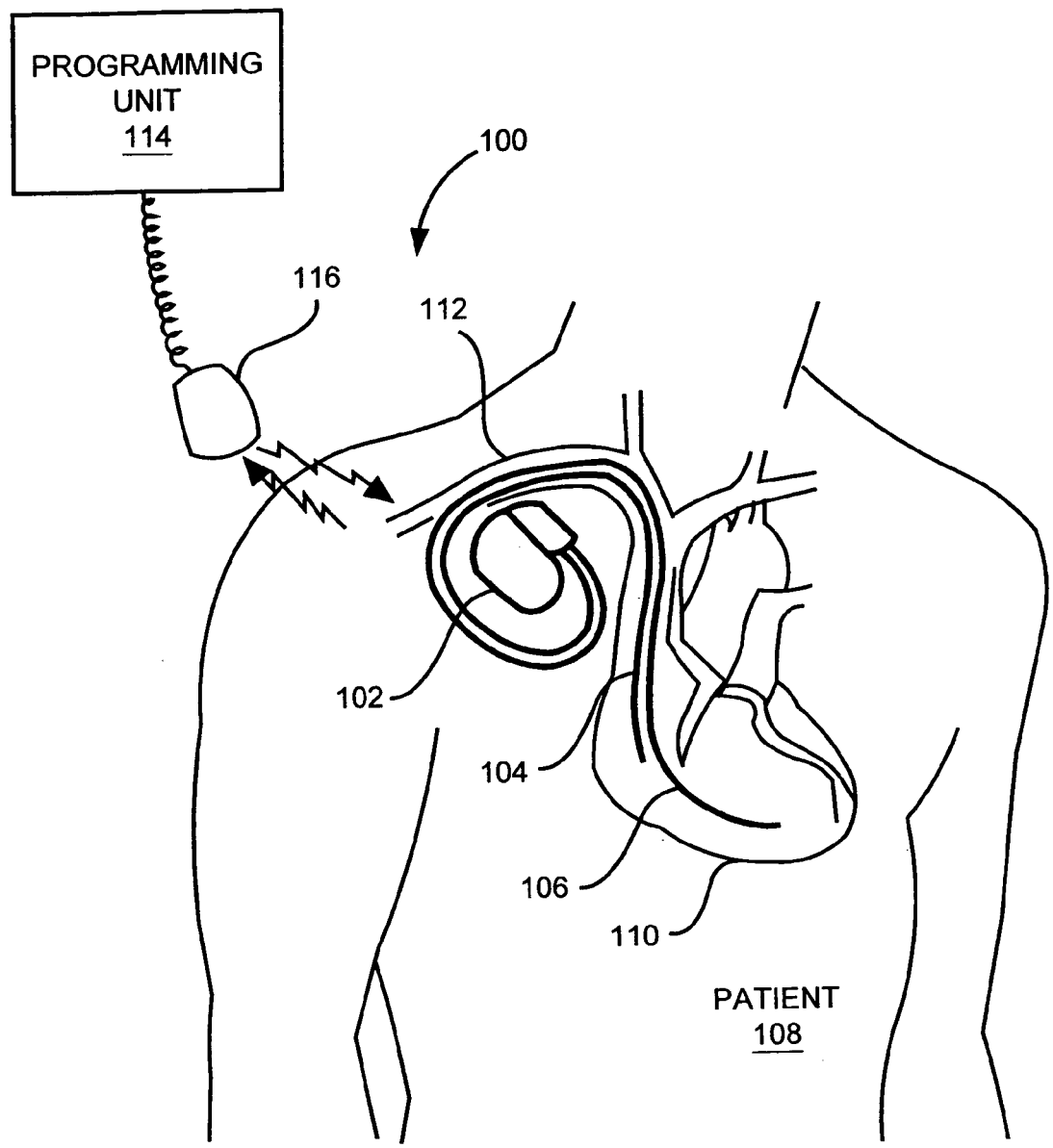
FIG. 1 is a diagram of one embodiment of an implantable medical device (IMD) system including a cardiac pacemaker, an atrial lead, and a ventricular lead implanted in a patient.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE PREFERRED EMBODIMENTS

Illustrative embodiments of the invention are described below. In the interest of clarity, not all features of an actual implementation are described in this specification. It will, of course, be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

FIG. 1 is a diagram of one embodiment of an implantable medical device (IMD) system 100 including a cardiac pacemaker 102, an atrial lead 104, and a ventricular lead 106 implanted in a patient 108. The pacemaker 102 produces electrical pulses (i.e., pacing pulses) that stimulate a heart 110 of the patient 108. One end of the atrial lead 104 is electrically coupled to the pacemaker 102, the other end of the atrial lead 104 extends through a vein 112 into a right atrium of the heart 110. One end of the ventricular lead 106 is electrically coupled to the pacemaker 102, the other end of the ventricular lead 106 extends through the vein 112 and into a right ventricle of the heart 110. Electrically conductive electrodes attached to the ends of the atrial lead 104 and the ventricular lead 106 located within the heart 110 are used to deliver pacing pulses to the heart 110, and to receive intrinsic electrical signals present within the heart 110.

The pacemaker 102 may be housed within a hermetically sealed, biologically inert outer canister or housing. At least a portion of the housing may be electrically conductive, and may serve as an electrode in pacing and/or sensing circuits of the pacemaker 102.

The IMD system 100 of FIG. 1 also includes a programming unit 114 for programming the pacemaker 102. A programming head 116 is connected to the programming unit 114, and enables two-way communication between the programming unit 114 and the pacemaker 102 as indicated in FIG. 1. For example, the programming head 116 may include a radio frequency (RF) antenna, and may send RF signals to, and receive RF signals from, the pacemaker 102.

Figure 2:
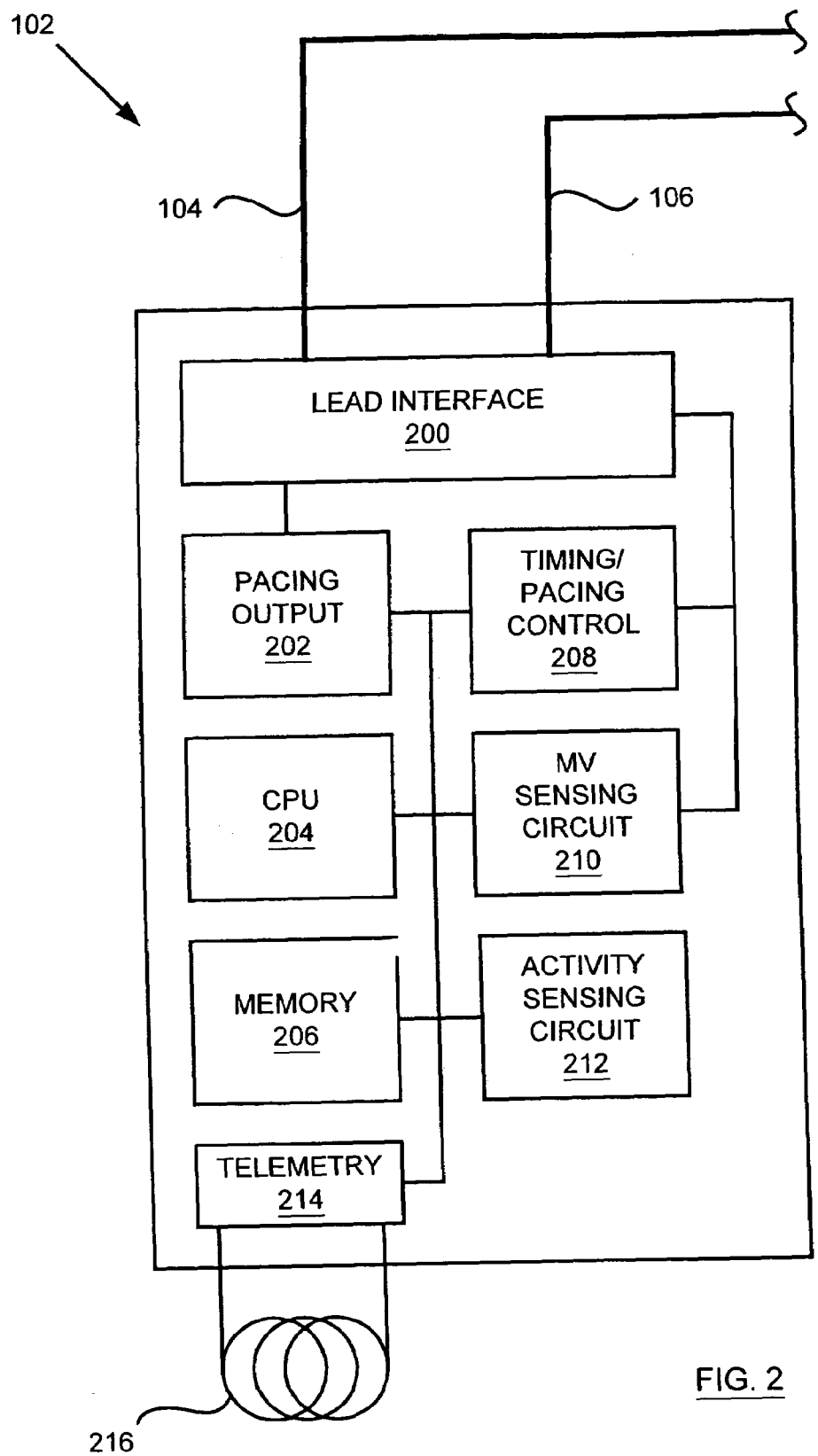
FIG. 2 is a diagram of one embodiment of the cardiac pacemaker of FIG. 1, wherein the pacemaker produces pacing pulses delivered to a heart of the patient of FIG. 1 via the atrial lead and the ventricular lead.
Figure 3A:
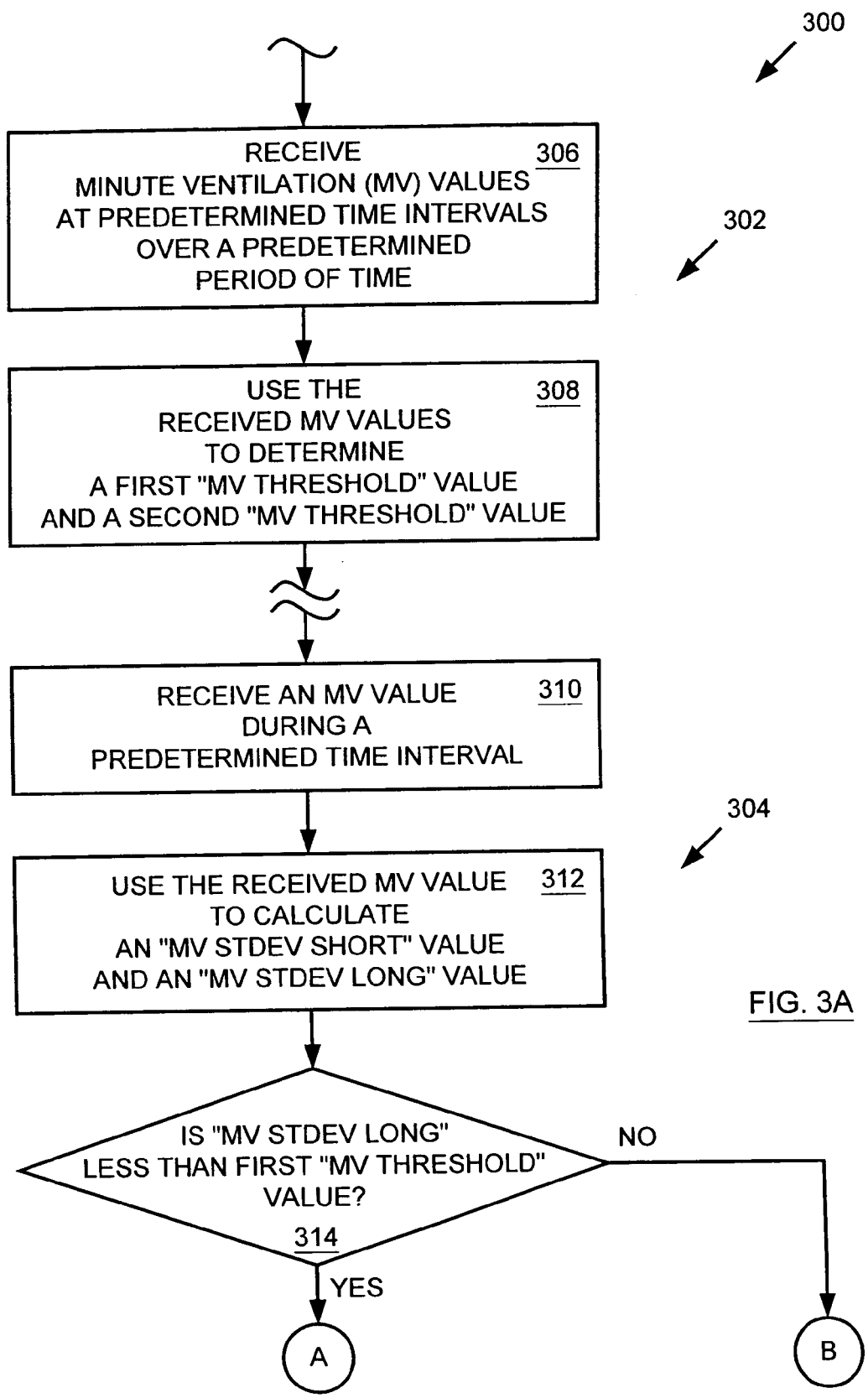
FIGS. 3A–3D in combination form a flow chart of one embodiment of a method for determining an onset of sleep in a patient having an implantable medical device (e.g., the pacemaker of FIGS. 1–2) implanted therein.
Figure 3B:
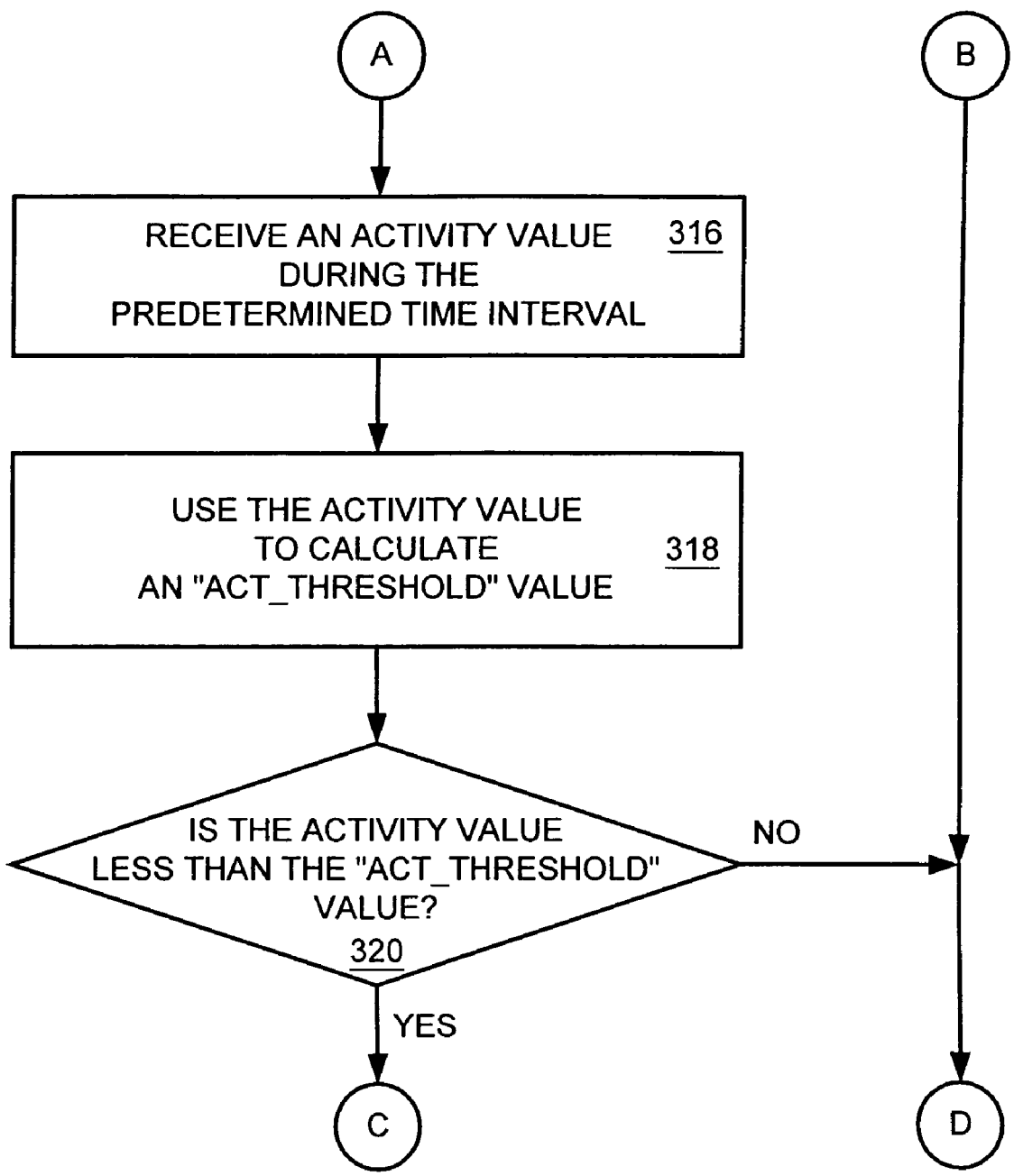
Figure 3C:
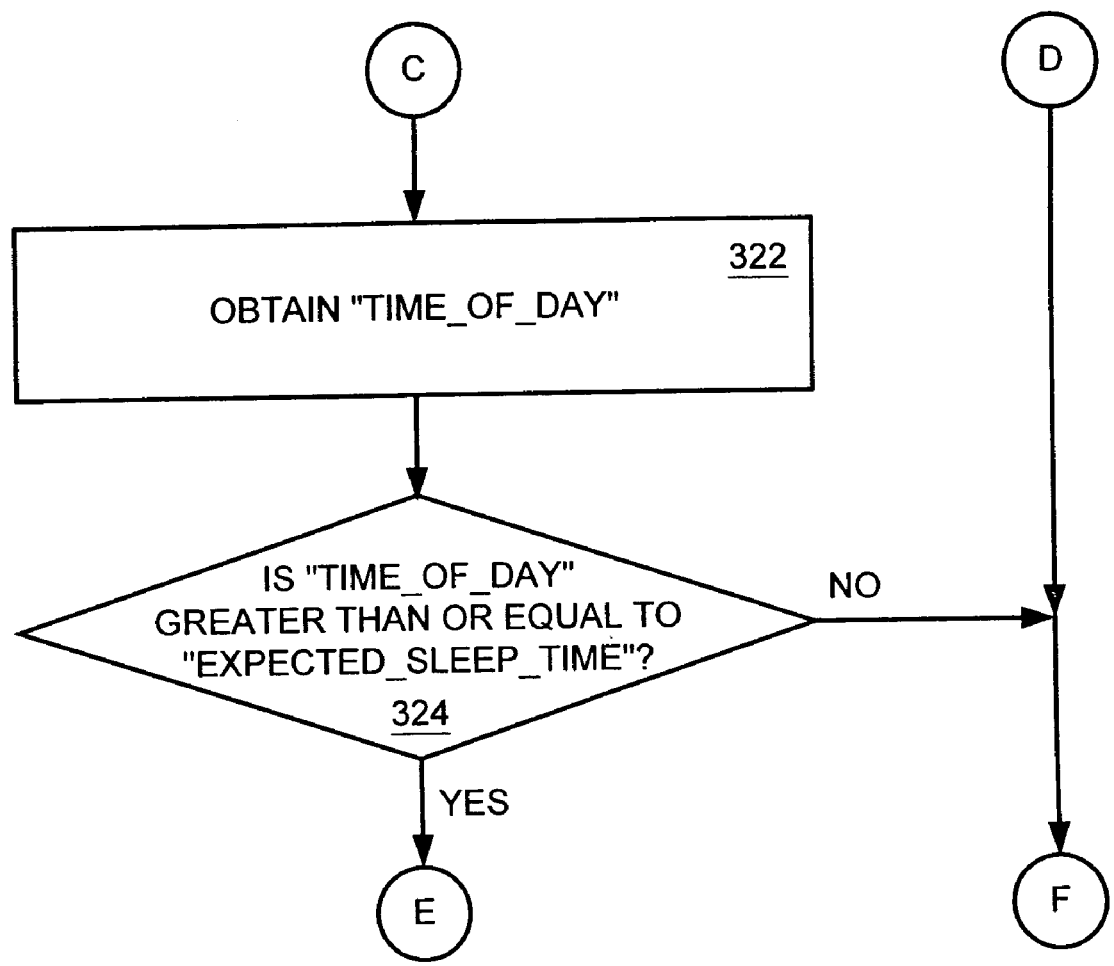
Figure 3D:
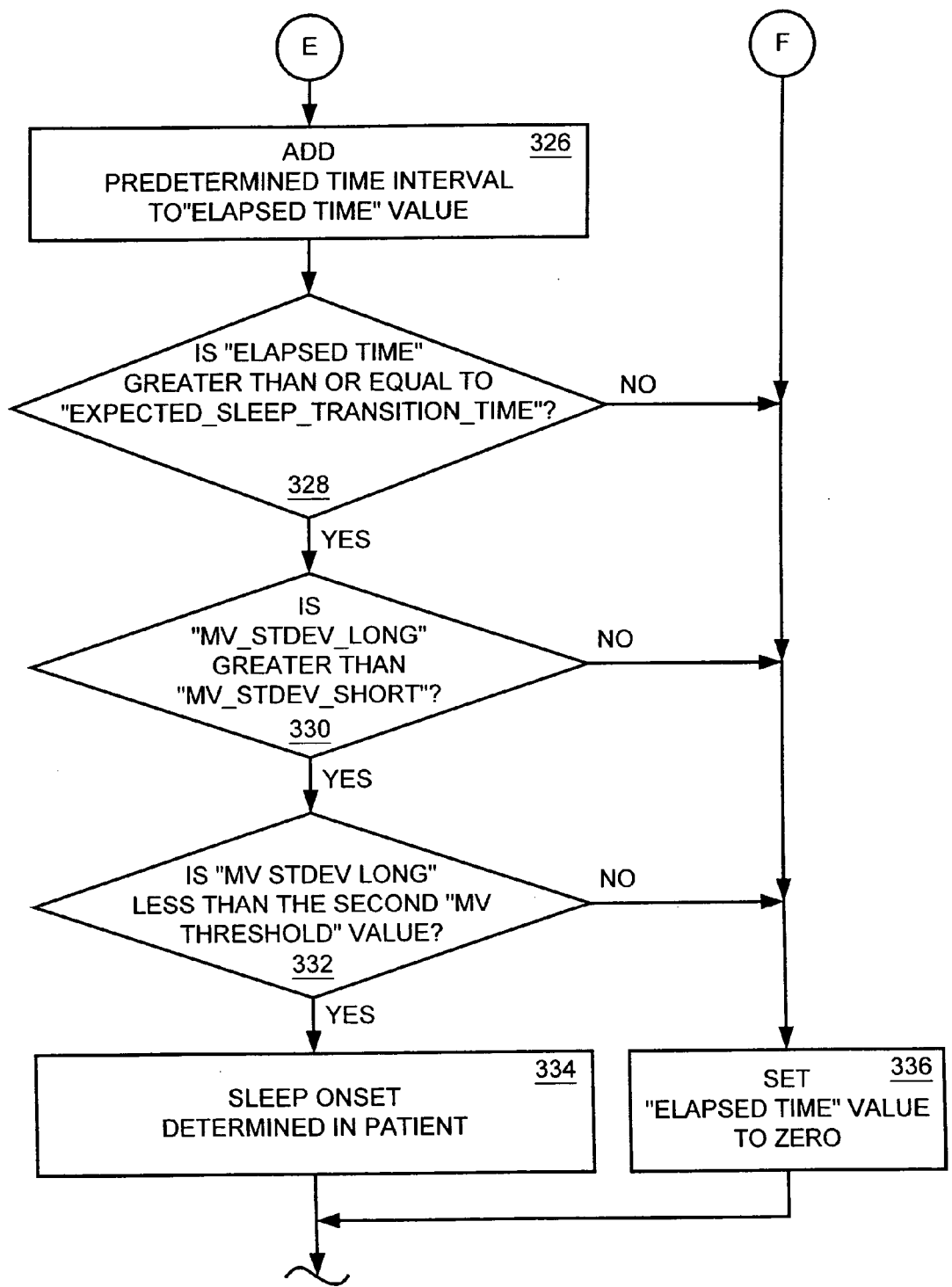

FIG. 2 is a diagram of one embodiment of the cardiac pacemaker 102 of FIG. 1. As described above, the pacemaker 102 produces pacing pulses delivered to the heart 110 of the patient 108 (FIG. 1) via the atrial lead 104 and the ventricular lead 106. In the embodiment of FIG. 2, the pacemaker 102 includes lead interface circuitry 200, pacing output circuitry 202, a central processing unit (CPU) 204, a memory 206, timing/pacing control circuitry 208, a minute ventilation (MV) sensing circuit 210, an activity sensing circuit 212, a telemetry unit 214, and an antenna 216.

The atrial lead 104 and the ventricular lead 106 conduct pacing pulses produced by the pacemaker 102 to the heart 110 of the patient 108 (FIG. 1), and also conduct intrinsic electrical signals present within the heart 110 to the pacemaker 102. The lead interface circuitry 200 forms an electrical interface between the atrial lead 104 and the ventricular lead 106 and other components of the pacemaker 102. As will be described in detail below, the pacing output circuitry 202 produces atrial and ventricular pacing pulses for stimulating the heart 110. The CPU 204 executes instructions stored in the memory 206, and controls the operations of other components of the pacemaker 102.

Adapted for connecting to the atrial lead 104 and the ventricular lead 106 and capable of delivering pacing pulses to the right atrium and the right ventricle of the heart 110 (FIG. 1), the pacemaker 102 of FIGS. 1 and 2 may be termed a "dual-chamber" pacemaker. The pacemaker 102 may be programmable to operate in one or more of several different predefined operating modes, including a "demand" mode. In the "demand mode," the pacemaker 102 senses intrinsic electrical signals present within the heart 110 of the patient 108 (FIG. 1), and produces pacing pulses only when the pacing pulses are needed. For example, the pacemaker 102 may be programmed with a value indicating whether or not the "demand" mode is enabled, a "low rate limit" value indicating a low limit of an intrinsic beat rate of the heart 110 of the patient 108 (FIG. 1), and an "atrioventricular (AV) interval" value indicating a maximum length of time between an atrial contraction or "atrial beat" and a subsequent ventricular contraction or "ventricular beat."

The timing/pacing control circuitry 208 may include various registers for storing values indicative of programmed parameters of the pacemaker 102, and various counters for performing timing functions. For example, the CPU 204 may store programmed "demand" mode, "low rate limit," and "AV interval" values in one or more registers of the timing/pacing control circuitry 208.

The timing/pacing control circuitry 208 includes sensing circuitry that receives and detects intrinsic electrical signals present within the heart 110 of the patient 108 (FIG. 1). Specifically, the sensing circuitry of the timing/pacing control circuitry 208 receives a first electrical signal indicative of an intrinsic contraction of the right atrium via the atrial lead 104. In response the first electrical signal, the sensing circuitry may generate an "atrial beat" signal within the timing/pacing control circuitry 208.

If the "demand" mode of the pacemaker 102 is enabled, the timing/pacing control circuitry 208 may provide an "atrial trigger" signal to the pacing output circuitry 202 if a frequency at which the "atrial beat" signals are generated is below the programmed "low rate limit." In other words, the timing/pacing control circuitry 208 may provide an "atrial trigger" signal to the pacing output circuitry 202 if the intrinsic beat rate of the heart 110 (FIG. 1) falls below the programmed "low rate limit." In response to the atrial trigger signal, the pacing output circuitry 202 may produce an atrial pacing pulse, and provide the atrial pacing pulse to the right atrium of the heart 110 (FIG. 1) via the atrial lead 104. The atrial pacing pulse typically causes the right and left atria of the heart 110 to contract in unison.

The sensing circuitry of the timing/pacing control circuitry 208 also receives a second electrical signal indicative of an intrinsic contraction of the right ventricle via the ventricular lead 106. In response the second electrical signal, the sensing circuitry may generate a "ventricular beat" signal within the timing/pacing control circuitry 208. If the "demand" mode of the pacemaker 102 is enabled and the "ventricular beat" signal is not generated within the programmed "AV interval" following an "atrial beat" signal, the timing/pacing control circuitry 208 may provide a "ventricular trigger" signal to the pacing output circuitry 202. In response to the "ventricular trigger" signal, the pacing output circuitry 202 may produce a ventricular pacing pulse, and provide the ventricular pacing pulse to the right ventricle of the heart 110 (FIG. 1) via the ventricular lead 106. The ventricular pacing pulse typically causes the right and left ventricles of the heart 110 to contract in unison.

The minute ventilation sensing circuit 210 produces a minute ventilation output signal indicative of the minute ventilation of the patient 108 (FIG. 1). In one embodiment, the minute ventilation sensing circuit 210 produces the minute ventilation output signal dependent upon changes of electrical impedance in a thoracic cavity of the patient 108, and the minute ventilation output signal constitutes digital values indicative of the minute ventilation of the patient 108 produced at regular time intervals. In other embodiments, the minute ventilation output signal may be a continuous analog signal.

As described above, electrically conductive electrodes are attached to the ends of the atrial lead 104 and the ventricular lead 106 (FIG. 1), and at least a portion of the outer canister or housing of the pacemaker 102 (FIGS. 1–2) may be electrically conductive. The minute ventilation sensing circuit 210 may deliver an electrical current excitation signal between a first electrode, at the end of either the atrial lead 104 or the ventricular lead 106, and the outer canister or housing of the pacemaker 102. The current excitation signal may include, for example, current pulses delivered at a predetermined rate (e.g., 16 pulses per second, or 16 Hertz). An electrical voltage signal may be measured between a second electrodes, at the end of the atrial lead 104 or the ventricular lead 106, and the outer canister or housing of the pacemaker 102. A thoracic impedance signal may be generated by dividing a magnitude of the electrical voltage signal by a magnitude of the electrical current excitation signal.

The thoracic impedance signal is a voltage signal having three main components: a direct current (d.c.) offset voltage, a cardiac component resulting from the function of the heart 110 of the patient 108 (FIG. 1), and a respiratory component. The minute ventilation sensing circuit 210 may include, for example, a bandpass filter (e.g., having a passband of, for example, 0.05 Hz to 0.8 Hz), and the thoracic impedance signal may be passed through the bandpass filter to substantially remove the d.c. offset voltage and the cardiac component. The resulting "filtered" thoracic impedance signal, emerging at an output of the bandpass filter, substantially comprises the respiratory component.

The minute ventilation sensing circuit 210 may also include sample-and-hold circuitry and comparison circuitry (not shown). As described above, the minute ventilation sensing circuit 210 may deliver current pulses at a predetermined rate (e.g., 16 Hz). The predetermined rate defines a time interval between pulses, referred to herein as a "cycle time." At the beginning of each cycle time, the minute ventilation sensing circuit 210 delivers a current pulse. The sample-and-hold circuitry may sample the filtered thoracic impedance signal at the beginning of each cycle time, thereby acquiring a "current" value of the filtered thoracic impedance signal. The comparison circuitry may compare the "current" value of the filtered thoracic impedance signal to a "previous" value of the filtered thoracic impedance signal, acquired by the sample-and-hold circuitry at the beginning of the preceding cycle time. The comparison circuitry may produce an analog "difference" voltage equal to a difference between the "current" value of the filtered thoracic impedance signal and the "previous" value of the thoracic impedance signal.

The minute ventilation sensing circuit 210 may also include analog-to-digital conversion circuitry, summing circuitry, and a register (not shown). The analog-to-digital conversion circuitry may convert the analog difference voltage produced by the comparison circuitry to a digital "count" value representing the difference between the "current" value of the filtered thoracic impedance signal and the "previous" value of the thoracic impedance signal at the beginning of the preceding cycle time. The summing circuitry may sum the digital "count" values produced by the analog-to-digital conversion circuitry over a predetermined number of the cycle times (i.e., over a predetermined time interval). The resulting sum of the digital "count" values, acquired over the predetermined time interval, is referred to herein as a "minute ventilation count value." A digital "minute ventilation count value" is thus present in the register at the end of each predetermined time interval, wherein the digital "minute ventilation count value" is indicative of the minute ventilation of the patient 108 (FIG. 1). At the end of each predetermined time interval, the digital "minute ventilation count value" (i.e., the contents of the register) may be provided to the CPU 204 (e.g., via an interrupt or programmed input/output mechanism), and the register may be cleared.

For example, the minute ventilation sensing circuit 210 may deliver current pulses at a rate of 16 Hz as described above. The summing circuitry may sum 32 of the digital "count" values produced by the analog-to-digital conversion circuitry over a predetermined 2-second time interval. At the end of each 2-second time interval, the digital "minute ventilation count value" (i.e., the contents of the register) may be provided to the CPU 204 (e.g., via an interrupt or programmed input/output mechanism), and the register may be cleared.

It is noted that there are several known methods for producing measures of minute ventilation of the patient 108 (FIG. 1), any one of which may be employed by the minute ventilation sensing circuit 210 to produce the minute ventilation output. For example, in other contemplated embodiments, the minute ventilation output may be a continuous analog waveform indicative of the minute ventilation of the patient 108 (FIG. 1). The continuous analog waveform may be sampled at regular intervals, and the analog samples may be converted to corresponding digital values.

The activity sensing circuit 212 senses movement or physical activity of the patient 108 (FIG. 1), and produces an "activity output" indicative of a magnitude of the movement or physical activity of the patient 108. In one embodiment, the "activity output" constitutes digital "activity values" produced at regular time intervals. In other embodiments, the "activity output" may be a continuous analog signal.

The activity sensing circuit 212 may include, for example, an element producing an electrical signal when subjected to mechanical stress (e.g., a piezoelectric crystal), and a mechanical apparatus for subjecting the element to mechanical stress when the patient 108 moves or is physically active. The element and the mechanical apparatus for subjecting the element to mechanical stress when the patient 108 moves or is physically active may form, for example, an accelerometer (not shown). The accelerometer may produce an output signal. Alternately, the activity sensing circuit 212 may include a piezoelectric sensor bonded to an inner surface of the outer canister or housing of the pacemaker 102 (FIGS. 1–2), and the piezoelectric sensor may produce the output signal.

The activity sensing circuit 212 may include a bandpass filter, and the output signal of the accelerometer or piezoelectric sensor may be coupled to an input of the bandpass filter. An output signal produced by the bandpass filter may be compared to a threshold value (e.g., a programmable threshold value). Peaks in the output signal of the bandpass filter which exceed the threshold value, referred to herein as "activity counts," may indicate movement or physical activity of the patient 108 (FIG. 1) of sufficient magnitude that an increase in pacing rate may be warranted.

The activity sensing circuit 212 may include circuitry for summing "activity counts" occurring within predetermined time intervals (e.g., two second time intervals), and a register for storing the sum of the "activity counts." At the end of each regular time interval, the corresponding sum of the "activity counts," contained within the register, constitutes a digital "activity value." The contents of the register may be provided to the CPU 204 at the end of each regular time interval (e.g., via an interrupt or programmed input/output mechanism), and the register may be cleared.

It is noted that there are several known methods for producing measures of movement or physical activity of the patient 108 (FIG. 1), any one of which may be employed by the activity sensing circuit 212 to produce the "activity output."

The pacemaker 102 is typically programmed with a "high rate limit" value indicating a high limit of an intrinsic beat rate of the heart 110 of the patient 108. If a "rate response" mode of the pacemaker 102 is enabled (e.g., via a programmable parameter), the CPU 204 may execute software instructions stored in the memory 206 that implement the "rate response" mode.

In this situation, the CPU 204 may vary the "low rate limit" value and/or the "AV interval" value stored in the timing/pacing control circuitry 208, dependent upon the minute ventilation output produced by the MV sensing circuit 210 and/or the activity output produced by the activity sensing circuit 212. the CPU 204 may vary the "low rate limit" value and/or the "AV interval" value according to a transfer function (e.g., a programmable transfer function) to achieve a rate response defined by the "low rate limit" value, the "high rate limit" value, and the transfer function. As a result, the rate at which the pacing output circuitry 202 produces the atrial pacing pulses is varied between the "low rate limit" and the "high rate limit" dependent upon the minute ventilation output produced by the MV sensing circuit 210 and/or the activity output produced by the activity sensing circuit 212. For example, a "target" pacing rate at which pacing output circuitry 202 produces the atrial pacing pulses may be expressed as:

"target"pacing rate="low rate limit"+*f*(sensing circuit output)

where f is a linear or monotonic function of the minute ventilation output produced by the MV sensing circuit 210 and/or the activity output produced by the activity sensing circuit 212.

For example, when the activity output produced by the activity sensing circuit 212 indicates that an activity level of the patient 108 (FIG. 1) has increased, the "target" pacing rate may be increased from the "low rate limit" by incremental amounts determined by the activity output produced by the activity sensing circuit 212. As long as the activity output produced by the activity sensing circuit 212 indicates activity of the patient 108, the "target" pacing rate may be periodically increased by incremental amounts until the "high rate limit" is reached. When the activity output produced by the activity sensing circuit 212 indicates activity of the patient 108 has ceased, the "target" pacing rate may be gradually reduced by incremental amounts until the "low rate limit" is reached.

The rate response function f is preferably selected such that the "target" pacing rate is based on a combination of the outputs of the activity sensing circuit 212 and the minute ventilation sensing circuit 210. For example, the rate response function f may be selected such that the "target" pacing rate is based substantially on the activity output produced by the activity sensing circuit 212 when the patient is relatively inactive, and based substantially on the minute ventilation output produced by the minute ventilation sensing circuit 210 when the patient is relatively active. Any one of several known methods for combining or "blending" outputs of activity sensors and minute ventilation sensors may be employed in generating the "target" pacing rate.

The telemetry unit 214 is coupled to the antenna 216, and communicates with the programming head 116 (FIG. 1) via antenna 216. For example, the antenna 216 may be a radio frequency (RF) antenna, and the telemetry unit 214 may send RF signals to, and receive RF signals from, the programming head 116 (FIG. 1). In the embodiment of FIGS. 1 and 2, CPU 204 communicates with the programming unit 114 (FIG. 1) via the telemetry unit 214, the antenna 216, and the programming head 116. CPU 204 receives values to be stored in memory locations of the memory 206 from the programming unit 114 via the telemetry unit 214. The received values may be, for example, the values of programmable parameters, which determine the operation of the pacemaker 102. CPU 204 may also use the telemetry unit 214 to transmit values residing in memory locations of the memory 206 to the programming unit 114. The transmitted values may be, for example, the values of programmable parameters, which determine the operation of the pacemaker 102, and/or data indicative of sensed parameters of the patient 108 (FIG. 1).

FIGS. 3A–3D in combination form a flow chart of one embodiment of a method 300 for determining an onset of sleep in a patient (e.g., patient 108 of FIG. 1) having an implantable medical device (e.g., pacemaker 102 of FIGS. 1–2) implanted therein. The method 300 may be embodied within software residing in the memory 206 (FIG. 2) of the pacemaker 102. The CPU 204 (FIG. 2) may carry out the method 300 when executing the software embodying the method 300.

The method 300 includes a "preliminary" portion 302 and a "recurrent" portion 304. During the preliminary portion 302, two minute ventilation threshold values are determined. At least some of the steps of the recurrent portion 304 are carried out at predetermined time intervals. The minute ventilation threshold values determined during the preliminary portion 302 are used during the recurrent portion 304 to determine the onset of sleep in a patient having the implantable medical device implanted therein.

During a step 306 of the preliminary portion 302, "minute ventilation values" are received at predetermined time intervals over a predetermined period of time. The minute ventilation values are indicative of the minute ventilation of the patient having the implantable medical device implanted therein. For example, in one embodiment of the minute ventilation sensing circuit 210 (FIG. 2) described above, the minute ventilation sensing circuit 210 delivers current pulses at a rate of 16 Hz, thereby defining pulse "cycles" having "cycle times" of $\frac{1}{16}$ or 0.0625 seconds. The minute ventilation sensing circuit 210 converts an analog difference voltage between a "current" value of a thoracic impedance signal, obtained during a "current" pulse cycle, and a "previous" value of the thoracic impedance signal, obtained during a pulse cycle preceding the current pulse cycle, to a digital "count" value. The minute ventilation sensing circuit 210 sums 32 of the digital "count" values produced by the analog-to-digital conversion circuitry in a register over a predefined 2-second time interval. The minute ventilation sensing circuit 210 provides a "minute ventilation value" contained in the register at the end of each 2-second time interval, then clears the register.

During a second step 308 of the preliminary portion 302, the minute ventilation values received during the step 306 are used to determine a first minute ventilation threshold value and a second minute ventilation threshold value. The first and second minute ventilation threshold values are used to determine a transition from an "awake" state of the patient to a "sleep" state of the patient. Due to the diurnal nature of the human wake-sleep cycle, the "predetermined period of time" in the step 306 is preferably at least 24 hours, and preferably a multiple of 24 hours, such that: (i) a first portion of the minute ventilation values received during the predetermined period of time are obtained when the patient is awake, (ii) a second portion of the minute ventilation values received during the predetermined period of time are obtained when the patient is asleep, and (iii) a ratio between the first portion and the second portion is representative of a wake-sleep cycle of the patient 108.

The first minute ventilation threshold value is greater than the second minute ventilation threshold value, and is used to screen the received minute ventilation value to determine if the carrying out of the remaining steps of the recurrent portion 304 is warranted. In calculating the first minute ventilation threshold value, a median value of the minute ventilation values received during the predetermined period of time is determined. The first minute ventilation threshold value is set to half the median value. The median value is substantially the "middle" minute ventilation value. That is, a number of the minute ventilation values received during the predetermined period of time are greater than the median value, and a substantially equal number of the minute ventilation values are less than the median value.

For example, during the step 306, the CPU 204 (FIG. 2) of the pacemaker 102 (FIGS. 1 and 2) may receive minute ventilation values from the minute ventilation sensing circuit 210 (FIG. 2) at 2-second intervals over a 24-hour period of time. Each time the CPU 204 receives a minute ventilation value, the CPU 204 may store the minute ventilation value in the memory 206 (FIG. 2). At the end of the 24-hour period of time, the CPU 204 may access the minute ventilation values stored in the memory 206, determine a median value of the minute ventilation values, and set the first minute ventilation threshold value to half the median value.

Alternately, the CPU 204 (FIG. 2) of the pacemaker 102 (FIGS. 1–2) may form a histogram of received minute ventilation values within the memory 206 (FIG. 2), and use the histogram to estimate the median value of the minute ventilation values. A range of expected minute ventilation values may be divided into equally-sized sub-ranges or "bins," and different memory locations of the memory 206 may be allocated for each of the bins. Each time the CPU 204 receives a minute ventilation value, the CPU 204 may determine which bin the minute ventilation value corresponds to, and add '1' to a running count maintained in the memory location allocated for that bin. At the end of the predetermined period of time (e.g., 24 hours), the CPU 204 may access the memory locations allocated for the bins, locate a bin wherein a number counts in bins above and below the bin are substantially equal, and select the median value within the sub-range of minute ventilation values represented by the bin. The CPU 204 may then set the first minute ventilation threshold value to half the selected median value.

Regarding the determining of the second minute ventilation value, the CPU 204 (FIG. 2) of the pacemaker 102 (FIGS. 1–2) may keep a running estimate of a mean value (i.e., an average value) of the received minute ventilation values. The mean value represents a "central tendency" of the received minute ventilation values. At the end of a predetermined time interval (i.e., after receiving a predetermined number of minute ventilation values), the CPU 204 may calculate a measure of deviation of the minute ventilation values received during the time interval from a "current" estimate of the mean value. The CPU 204 may form a histogram of the deviations of the minute ventilation values from the mean value.

As further described below, a histogram of deviations of minute ventilation values from a mean value, formed over a "sleep-wake" cycle of the patient, has a first peak representing deviations of minute ventilation values from the mean value when the patient is asleep, a second peak representing deviations of minute ventilation values from the mean value when the patient is awake, and a "trough" between the first and second peaks representing deviations of minute ventilation values from the mean value when the patient is transitioning between the "awake" state and the "sleep" state. The CPU 204 may select a value for the second minute ventilation threshold value between the first and second peaks of the histogram.

For example, the CPU 204 (FIG. 2) may calculate a standard deviation of minute ventilation values received during predetermined time intervals (i.e., time "windows"), and may form a histogram of resulting minute ventilation standard deviation values within the memory 206 (FIG. 2). A range of expected minute ventilation standard deviation values may be divided into equally-sized sub-ranges or "bins," and different memory locations of the memory 206 may be allocated for each of the bins. At the end of each time window, the CPU 204 may calculate the minute ventilation standard deviation value, determine which bin the minute ventilation standard deviation value corresponds to, and add '1' to a running count maintained in the memory location allocated for that bin. At the end of the predetermined period of time (e.g., 24 hours), the CPU 204 may access the memory locations allocated for the bins. The CPU 204 may locate a bin having a lowest count between two other bins having the highest counts. The two bins having the highest counts include a bin of the first peak and a bin of the second peak, and the bin having the lowest count in between the first and second peaks is a bin of the trough of the histogram.

As further described below, the CPU 204 may select the second minute ventilation threshold value as a value (e.g., a minimum value) within the sub-range of minute ventilation values represented by the bin having the lowest count. Alternately, the CPU 204 may select the second minute ventilation threshold value as a value (e.g., a minimum value) within a sub-range of minute ventilation values represented by a bin between the bin having the lowest count and the bin of the first peak having one of the two highest count. Further, The CPU 204 may select the second minute ventilation threshold value as a value (e.g., a minimum value) within a sub-range of minute ventilation values represented by a bin midway between the bins of the first and second peaks and having the two highest counts.

As described above, at least some of the steps of the recurrent portion 304 are carried out at predetermined time intervals. During a step 310 of the recurrent portion 304, a minute ventilation value is received during one of the predetermined time intervals. The minute ventilation value is used to calculate an "MV Stdev Short" value and an "MV Stdev Long" value. The "MV Stdev Short" value is a standard deviation of minute ventilation values received during m time intervals including the current time interval and an immediately preceding m−1 time intervals. The "MV Stdev Long" value is a standard deviation of minute ventilation values received during n time intervals including the current time interval and the immediately preceding n−1 time intervals. In general, n≧m; however, for improved performance, n is preferably greater than m. For example, the value of m may be selected such that the "MV Stdev Short" value is calculated over a 2–5 minute period of time, and the value of n may be selected such that the "MV Stdev Long" value is calculated over a 10–15 minute period of time.

As described above, the minute ventilation sensing circuit 210 (FIG. 2) may produce a new minute ventilation value at the end of predetermined time intervals (e.g., 2-second time intervals). The CPU 204 (FIG. 2) may keep a running estimates of mean values (i.e., average values) of minute ventilation values received during various predetermined periods of time or time "windows." The CPU 204 may update the running estimates of the mean values each time a new minute ventilation value is produced by the minute ventilation sensing circuit 210 using:

$$\text{Mean}(i) = MV(i)/p + \text{Mean}(i-1) - \text{Mean}(i-1)/p$$

where Mean(i) is the mean value estimate during an ith time interval, MV(i) is the minute ventilation value produced the minute ventilation sensing circuit 210 during the ith time interval, p is the total number of elapsed time intervals, and Mean(i−1) is the mean value estimate during the time interval immediately preceding the ith time interval.

Regarding calculation of the "MV Stdev Short" value during a "current" time interval k, a mean value estimate Mean(k) value may be calculated using the minute ventilation values received during the current time interval and an immediately preceding m−1 time intervals (i.e., p=m), and the "MV Stdev Short" value may be calculated using:

$$MVStdevShort = \sqrt{\frac{\sum_{j=1}^{m}(MV(k-m-j)-Mean(k))^2}{m}}$$

Regarding calculation of the "MV Stdev Long" value during a "current" time interval k, a mean value estimate Mean(k) value may be calculated using the minute ventilation values received during the current time interval and an immediately preceding n−1 time intervals (i.e., p=n), and the "MV Stdev Long" value may be calculated using:

$$MVStdevLong = \sqrt{\frac{\sum_{j=1}^{n}(MV(k-n-j)-Mean(k))^2}{n}}$$

For example, the CPU 204 (FIG. 2) of the pacemaker 102 (FIGS. 1–2) may receive minute ventilation values at 2-second time intervals, and memory locations of the memory 206 (FIG. 2) may be allocated for minute ventilation values obtained during the immediately preceding n−1 2-second time intervals. During the step 312, the CPU 204 (FIG. 2) of the pacemaker 102 (FIGS. 1–2) may receive a "current" minute ventilation value, and access the memory locations allocated for the minute ventilation values obtained during the immediately preceding n−1 2-second time intervals. The CPU 204 may use the "current" minute ventilation value and the minute ventilation values obtained over the immediately preceding m−1 time intervals to compute the "MV Stdev Short" value. The CPU 204 may also use the "current" minute ventilation value and the minute ventilation values obtained over the immediately preceding n−1 time intervals to compute the "MV Stdev Long" value.

During a decision step 314, the "MV Stdev Long" value is compared to the first minute ventilation threshold value determined during the step 308. If the "MV Stdev Long" value is less than the first minute ventilation threshold value, an optional step 316 may be accomplished. On the other hand, if the "MV Stdev Long" value is greater than or equal to the first minute ventilation threshold value, a step 336 is accomplished. During the step 336, an "elapsed time" value is set to zero, and the recurrent portion 304 of the method 300 is exited.

Steps 316–320 represent an optional "activity cross-check" section of the recurrent portion 304 of the method 300. Steps 316–320 are believed to enhance performance of the method 300, but need not be accomplished for method 300 to work. During the optional step 316, an "activity value" is received during the predetermined time interval, wherein the activity value is indicative of a degree of movement of the patient during the predetermined time interval.

For example, the CPU 204 (FIG. 2) of the pacemaker 102 (FIGS. 1 and 2) may receive activity values from the activity sensing circuit 212 (FIG. 2) at 2-second intervals. The activity sensing circuit 212 may include and accelerometer, a bandpass filter, comparison circuitry, summing circuitry, and a register. An output signal of the accelerometer may be passed through the bandpass filter, and the resultant filtered output signal provided to the comparison circuitry. The comparison circuitry may compare the filtered output signal to a threshold value (e.g., a programmable threshold value). Peaks in the filtered output signal, which exceed the threshold value, are referred to herein as "activity counts." The summing circuitry may sum the "activity counts" occurring within a 2-second time interval in the register. At the end of each 2-second time interval, the activity sensing circuit 212 may provide the digital sum of the "activity counts" contained in the register, constituting the "activity value," and the register may be cleared.

During the optional step 318, the activity value is used to calculate an "ActThreshold" value, wherein the "ActThreshold" value is a sum of all "activity values" obtained during q time intervals including the current time interval and an immediately preceding q−1 time intervals. The value of q may be, for example, 20. The "ActThreshold" value during a "current" time interval k may be expressed as:

$$\text{ActThreshold} = \Sigma_{j=1}^{q} MV(k-q-j)$$

where MV(i) is the minute ventilation value produced the minute ventilation sensing circuit 210 during the ith time interval.

During the optional decision step 320, the activity value and the "ActThreshold" value calculated during the step 318 are compared. If the activity value is less than the "ActThreshold" value, an optional step 322 may be accomplished. On the other hand, if the activity value is greater than or equal to the "ActThreshold" value, the step 336 is accomplished. As described above, during the step 336, the "elapsed time" value is set to zero, and the recurrent portion 304 of the method 300 is exited.

Steps 322–324 represent an optional "time-of-day crosscheck" section of the recurrent portion 304 of the method 300. Steps 322–324 are believed to enhance performance of the method 300, but need not be accomplished for method 300 to work. During the optional step 322, a "TimeofDay" value is obtained, wherein the "TimeofDay" value is indicative of a current time of day. During the optional decision step 324, the "TimeofDay" value is compared to a predetermined "ExpectedSleepTime" value, wherein the "ExpectedSleepTime" value is indicative of a time of day the patient is expected to go to sleep each day. The "ExpectedSleepTime" value may be, for example, a programmable value. If the "TimeofDay" value is greater than or equal to the "ExpectedSleepTime" value, an optional step 322 may be accomplished accomplished. On the other hand, if the "TimeofDay" value is less than the "ExpectedSleepTime" value, the step 336 is accomplished. As described above, during the step 336, the "elapsed time" value is set to zero, and the recurrent portion 304 of the method 300 is exited.

During a step 326, a length of the predetermined time interval is added to the "Elapsed Time" value. The "Elapsed Time" value is compared to an "ExpectedSleepTransitionTime" value during a decision step 328, wherein the "ExpectedSleepTransitionTime" value is a period of time allotted for the patient to transition from the "awake" state to the "sleep" state. The "ExpectedSleepTime" value may be, for example, a programmable value. If the "Elapsed Time" value is greater than or equal to the "ExpectedSleepTransitionTime" value, a decision step 330 is accomplished. On the other hand, if the "Elapsed Time" value is less than the "ExpectedSleepTransitionTime" value, the step 336 is accomplished. As described above, during the step 336, the "elapsed time" value is set to zero, and the recurrent portion 304 of the method 300 is exited.

During the decision step 330, the "MV Stdev Long" value is compared to the "MV Stdev Short" value. If the "MV Stdev Long" value is greater than or equal to the "MV Stdev Short" value, a decision step 332 is accomplished. On the other hand, if the "MV Stdev Long" value is less than the "MV Stdev Short" value, the step 336 is accomplished.

The decision step 330 enhances the method 300 by detecting abrupt transitions from the "sleep" state to the "awake" state. Typically, as the patient transitions from the "awake" state to the "sleep" state, the patient's minute ventilation decreases monotonically over time. Thus while the patient is sleeping, the "MV Stdev Long" value is typically greater than or equal to the "MV Stdev Short" value. However, when the patient wakes up abruptly and becomes active, the "MV Stdev Short" value will become greater than the "MV Stdev Long" value, indicating the patient has transitioned from the "sleep" state to the "awake" state.

During the decision step 332, the "MV Stdev Long" value and the second minute ventilation threshold value, calculated during the step 308, are compared. If the "MV Stdev Long" value is less than the second minute ventilation threshold value, a step 334 is accomplished. On the other hand, if the "MV Stdev Long" value is greater than or equal to the second minute ventilation threshold value, the step 336 is accomplished. As described above, during the step 336, the "elapsed time" value is set to zero, and the recurrent portion 304 of the method 300 is exited. During the step 334, the patient is determined to have transitioned from the "awake" state to the "sleep" state.

Figure 4:
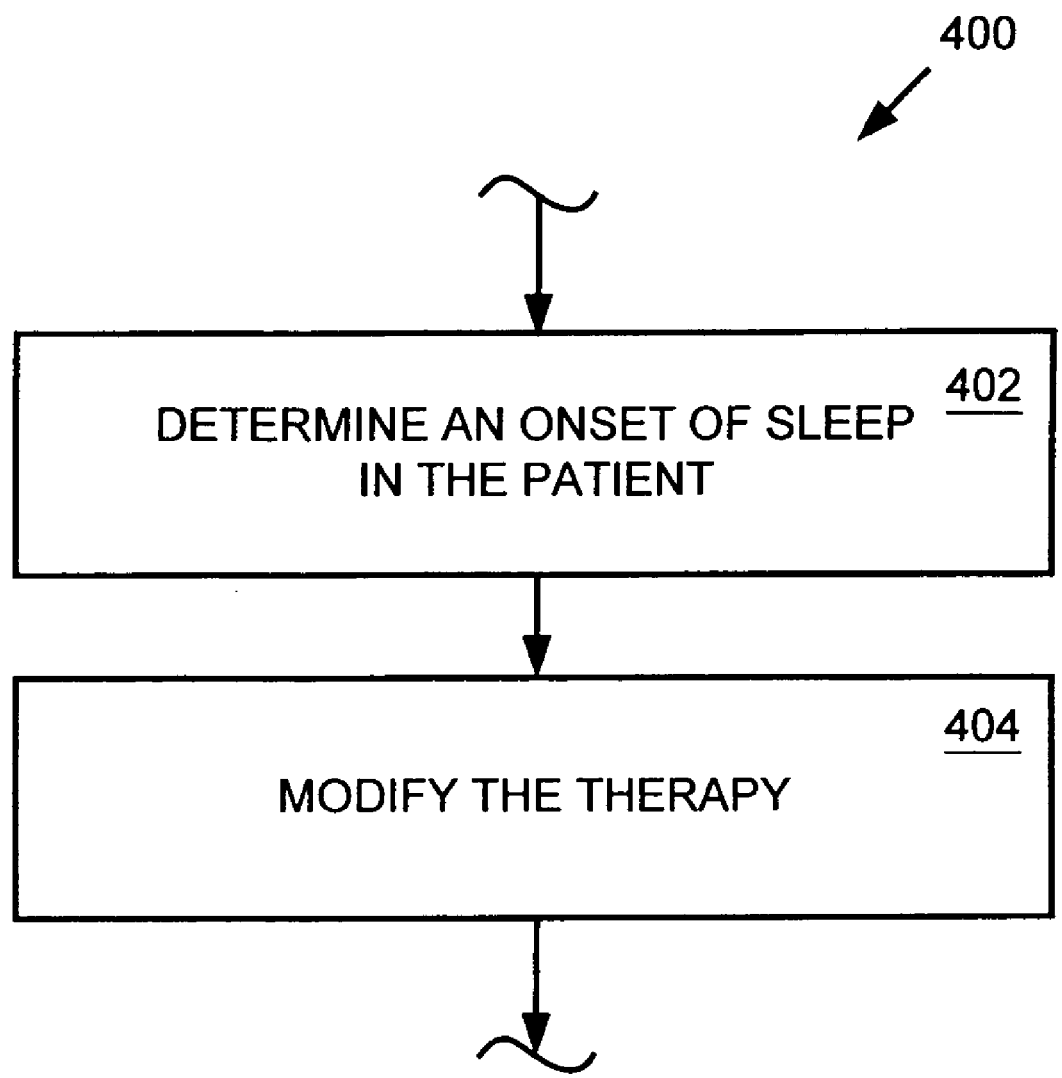
FIG. 4 is a flow chart of one embodiment of a method for providing a therapy to the patient, wherein the method involves determining an onset of sleep in the patient.

FIG. 4 is a flow chart of one embodiment of a method 400 for providing a therapy to a patient (e.g., the patient 108 of FIG. 1). The method 400 may be embodied within software residing in the memory 206 (FIG. 2) of the pacemaker 102 (FIGS. 1–2). The CPU 204 (FIG. 2) may carry out the method 400 when executing the software embodying the method 400. During a first step 402 of the method 400, an onset of sleep is determined in the patient. The step 402 of the method 400 may be accomplished by carrying out the steps of the method 300 of FIGS. 3A–3D. During a step 404, the therapy provided to the patient is modified.

For example, in the embodiment of FIG. 1, the patient 108 has the pacemaker 102 implanted therein, and the atrial lead 104 and the ventricular lead 106 extend from the pacemaker 102 and into the heart 110 of the patient 108. In the embodiment of FIG. 2, the pacemaker 102 includes the pacing output circuitry 202, the CPU 204, and the timing/pacing control circuitry 208. The pacing output circuitry 202 produces atrial and ventricular pacing pulses for stimulating the heart 110. The CPU 204 may store programmable "demand" mode, "low rate limit," and "AV interval" values in one or more registers of the timing/pacing control circuitry 208.

The timing/pacing control circuitry 208 includes sensing circuitry that receives and detects intrinsic electrical signals present within the heart 110 of the patient 108. Specifically, the sensing circuitry of the timing/pacing control circuitry 208 receives a first electrical signal indicative of an intrinsic contraction of the right atrium via the atrial lead 104. In response the first electrical signal, the sensing circuitry may generate an "atrial beat" signal within the timing/pacing control circuitry 208.

If the "demand" mode of the pacemaker 102 is enabled, the timing/pacing control circuitry 208 may provide an "atrial trigger" signal to the pacing output circuitry 202 if a frequency at which the "atrial beat" signals are generated is below the programmed "low rate limit." In other words, the timing/pacing control circuitry 208 may provide an "atrial trigger" signal to the pacing output circuitry 202 if the intrinsic beat rate of the heart 110 falls below the programmed "low rate limit." In response to the atrial trigger signal, the pacing output circuitry 202 may produce an atrial pacing pulse, and provide the atrial pacing pulse to the right atrium of the heart 110 via the atrial lead 104.

The CPU 204 may embody the above described method 300 for detecting onsets of sleep in the patient 108, and/or the method 400 for providing a therapy to a patient. For example, having detected an onset of sleep in the patient 108 (e.g., during the step 334 of the method 300), the CPU 204 may reduce the "low rate limit" value stored in the timing/pacing control circuitry 208 from a normal "resting rate" value (e.g., 60 beats per minute) to a "sleep rate" value, wherein the "sleep rate" value is less than or equal to the "resting rate." The "sleep rate" value may be, for example, a programmable value. The "sleep rate" value may be, for example, between 50 beats per minute and 60 beats per minute.

The above described methods 300 and 400 may also be useful for other purposes than reducing "low rate limit" values from normal "resting rate" values to "sleep rate" values in pacemakers. For example, the method 300 may be used to detect onsets of sleep for monitoring sleep-related events (i.e. sleep apnea, etc.), and the method 400 may be used in providing other medical therapies (e.g., electrical shocks for treating atrial fibrillation, administration of medications, etc.).

Figure 5A:
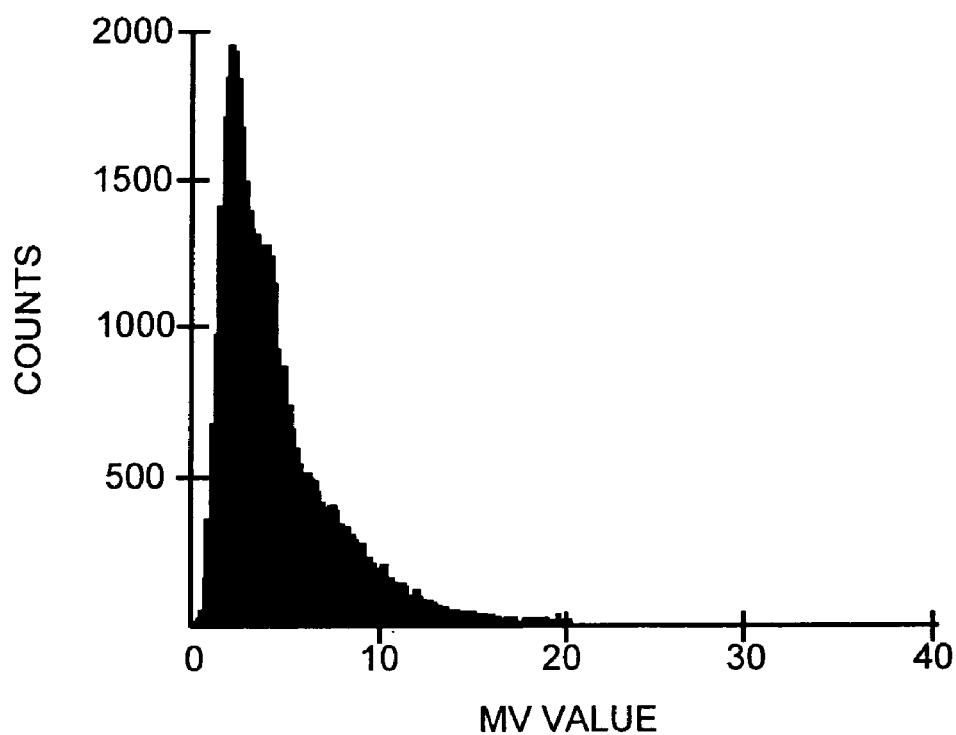
FIG. 5A is a histogram of minute ventilation values of a patient obtained via minute ventilation sensing circuitry over a 24-hour period.
Figure 5B:
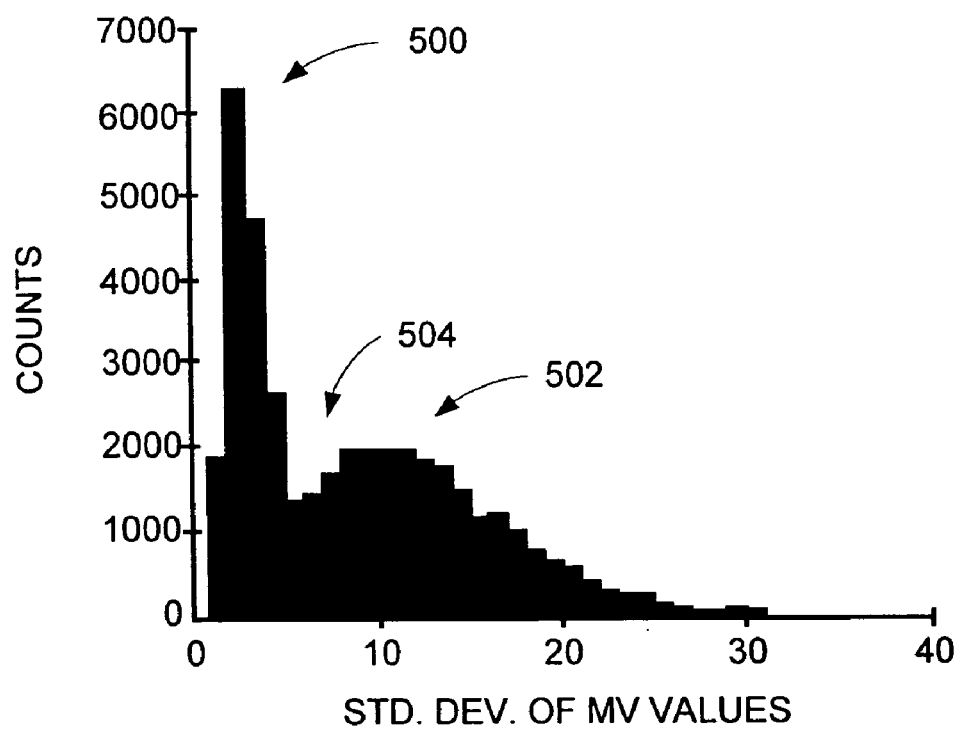
FIG. 5B is a histogram of standard deviations of the minute ventilation values used to form the histogram of FIG. 4A and received within 1-minute time windows.

FIGS. 5A and 5B will now be used to further describe the calculation of the second minute ventilation threshold value. FIG. 5A is a histogram of minute ventilation values of a patient obtained via minute ventilation sensing circuitry over a 24-hour period. In obtaining data for the histogram of FIG. 5A, minute ventilation sensing circuitry delivered current pulses at a rate of 16 Hz, thereby defining pulse "cycles" having "cycle times" of 1/16 or 0.0625 seconds. The minute ventilation sensing circuitry converted an analog difference voltage between a "current" value of a thoracic impedance signal, obtained during a "current" pulse cycle, and a "previous" value of the thoracic impedance signal, obtained during a pulse cycle immediately preceding the current pulse cycle, to a digital "count" value. The minute ventilation sensing circuitry summed 32 of the digital "count" values produced by the analog-to-digital conversion circuitry in a register over predefined 2-second time intervals. At the end of each 2-second time interval, the minute ventilation sensing circuitry produced a "minute ventilation value" contained in the register, and the register is cleared.

A range of expected minute ventilation values was divided into equally-sized sub-ranges or "bins," and different memory locations of a memory were allocated for each of the bins. Each time a minute ventilation value was produced by the minute ventilation sensing circuitry, a determination was made as to which bin the minute ventilation value corresponds to, and a '1' was added to a running count maintained in the memory location allocated for that bin. At the end of the 24-hour period, the running counts maintained in the memory locations allocated for the bins were read out.

FIG. 5B is a histogram of standard deviations of the minute ventilation values used to form the histogram of FIG. 5A and received within 1-minute time windows. As described above, the minute ventilation sensing circuitry produced a new minute ventilation value at the end of each 2-second time interval. A running estimate of a mean of the minute ventilation values was updated each time a new minute ventilation value was produced by the minute ventilation sensing circuitry as described above. At the end of each 1-minute time window, ending with a 2-second time interval k, a mean value estimate Mean(k) was calculated using the minute ventilation values received during the current time interval and an immediately preceding 29 time intervals (i.e., p=30) as described above, and the standard deviation of the 30 minute ventilation values received during the time window was calculated using:

$$MVStdev = \sqrt{\frac{\sum_{j=1}^{30}(MV(k-30-j) - Mean(k))^2}{30}}$$

The histogram of FIG. 5B was formed within a memory. A range of expected minute ventilation standard deviation values was divided into equally-sized sub-ranges or "bins," and different memory locations of the memory were allocated for each of the bins. At the end of each 1-minute time window, the corresponding minute ventilation standard deviation value was calculated. A determination was made as to which bin the minute ventilation standard deviation value corresponded to, and '1' was added to a running count maintained in the memory location allocated for that bin. At the end of the 24-hour time period, the contents of the memory locations allocated for the bins were read out.

The histogram of FIG. 5B has a first peak 500, a second peak 502, and "trough" 504 located between the first peak 502 and the second peak 504. The first peak 500 represents a portion of the minute ventilation values produced by the minute ventilation sensing circuit 210 when the patient is asleep. The second peak 502 represents a different portion of the minute ventilation values produced by the minute ventilation sensing circuit 210 when the patient is awake.

Regarding use of the histogram of FIG. 5B to determine the second minute ventilation threshold value, the second minute ventilation threshold value may be selected from among the minute ventilation values located in the trough 504. For example, the second minute ventilation threshold value may be selected as a value (e.g., a minimum value) within the sub-range of minute ventilation values represented by the bin having the lowest count (i.e., a bin having the lowest count within the trough 504.). Alternately, the second minute ventilation threshold value may be selected as a value (e.g., a minimum value) within a sub-range of minute ventilation values represented by a bin between the bin having the lowest count within the trough 504 and a bin of the first peak 500 having the highest count. Further, the second minute ventilation threshold value may be selected as a value (e.g., a minimum value) within a sub-range of minute ventilation values represented by a bin midway between a bin of the first peak 500 having a highest count, and a bin of the second peak 502 having a highest count.

Figure 6:
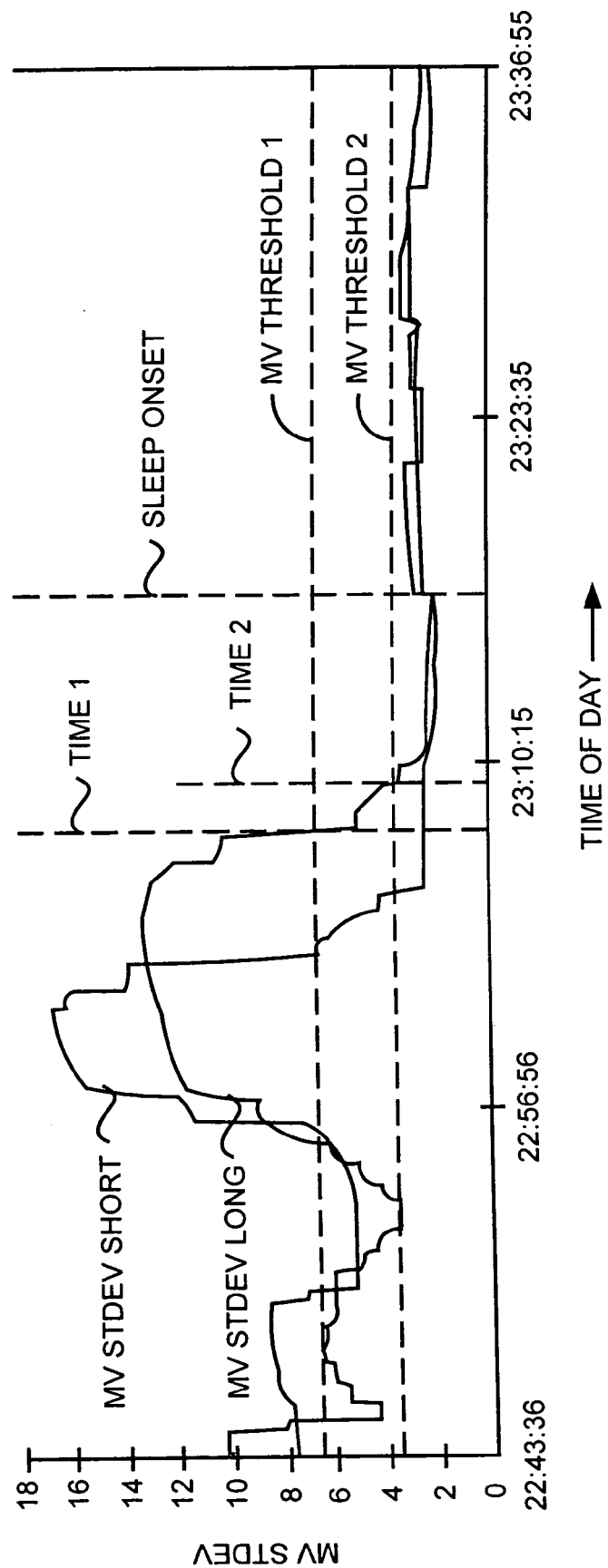
FIG. 6 is a graph of standard deviation values "MV Stdev Long" and "MV Stdev Short" calculated using minute ventilation values produced during 2-second time intervals and indicative of the minute ventilation of a patient.

FIG. 6 is a graph of "MV Stdev Long" and "MV Stdev Short" values described above, wherein the "MV Stdev Long" and "MV Stdev Short" values were calculated using minute ventilation values produced during 2-second time intervals and indicative of the minute ventilation of a patient. In FIG. 6, the first minute ventilation threshold value described above defines an "MV Threshold 1" level, and the second minute ventilation threshold value described above defines an "MV Threshold 2" level. As illustrated in FIG. 6, the "MV Threshold 1" level is greater than the "MV Threshold 2" level. As described above, the first minute ventilation threshold value is used to screen a received minute ventilation value to determine if the received minute ventilation value is sufficiently low as to warrant further analysis to detect an onset of sleep.

A time of day labeled "Sleep Onset" in FIG. 6 is a time the method 300 of FIGS. 3A–3D determine an onset of sleep in the patient. Prior to the "Sleep Onset" time, the "MV Stdev Short" and "MV Stdev Long" values drop below the "MV Threshold 1" level several times, and occasionally drop below the "MV Threshold 2" level, indicating a decrease in patient activity and an impending transition from an "awake" state to a "sleep" state. At a time of day labeled "Time 1" in FIG. 6, prior to the "Sleep Onset" time, the "MV Stdev Long" value drops below the "MV Threshold 1" level, thus indicating received minute ventilation values are sufficiently low as to warrant further analysis to detect an onset of sleep. (See the step 314 of the method 300, FIG. 3A.) At a time of day labeled "Time 2" in FIG. 6, between the "Time 1" and "Sleep Onset" times, the "MV Stdev Long" value drops below the "MV Threshold 2" level, and remains below the "MV Threshold 2" level for all subsequent times of day. The "Sleep Onset" time occurs a period of time after "Time 2" equal to the "ExpectedSleepTransitionTime" described above. (See the step 328 of the method 300, FIG. 3D.)

Figure 7:
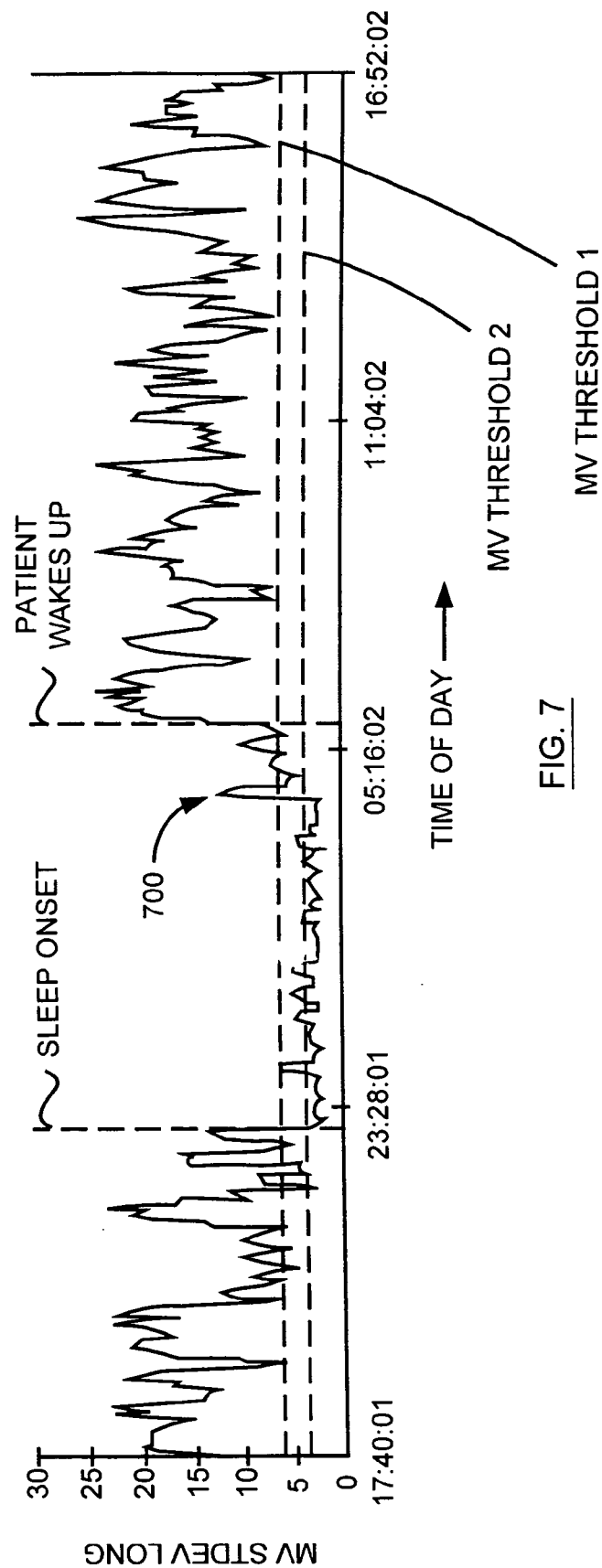
FIG. 7 is a graph of a standard deviation value "MV Stdev Long" calculated using minute ventilation values produced during 2-second time intervals and indicative of the minute ventilation of a patient.

FIG. 7 is a graph of "MV Stdev Long" values described above, wherein the "MV Stdev Long" values were calculated using minute ventilation values produced during 2-second time intervals and indicative of the minute ventilation of a patient. As in FIG. 6, the first minute ventilation threshold value described above defines a level labeled "MV Threshold 1," and the second minute ventilation threshold value described above defines a level labeled "MV Threshold 2."

A time of day labeled "Sleep Onset" in FIG. 7 is a time the method 300 of FIGS. 3A–3D determine an onset of sleep in the patient. Prior to the "Sleep Onset" time, the "MV Stdev Long" value substantially remains above the "MV Threshold 1" and "MV Threshold 2" levels, indicating a relatively high level of patient activity characteristic of an "awake" state of the patient. Just prior to the "Sleep Onset" time, the "MV Stdev Long" value drops below the "MV Threshold 1" level several times, and occasionally drops below the "MV Threshold 2" level, indicating a decrease in patient activity and an impending transition from the "awake" state to a "sleep" state. At the "Sleep Onset" time, the "MV Stdev Long" value has dropped below the "MV Threshold 2" level for a period of time equal to the "ExpectedSleepTransitionTime" described above. (See the step 328 of the method 300, FIG. 3D.)

The patient woke up at a time of day labeled "Patient Wakes Up" in FIG. 7. At various times between the "Sleep Onset" time and the time labeled "Patient Wakes Up" in FIG. 7, the "MV Stdev Long" value rises above the "MV Threshold 2" level, but does not rise above the "MV Threshold 1" level. A peak 700 in the "MV Stdev Long" value, exceeding the "MV Threshold 1" level, occurs around a time the patient got out of bed briefly. Between a time of day corresponding to the peak 700 and the time labeled "Patient Wakes Up" in FIG. 7, the "MV Stdev Long" value is above the "MV Threshold 2" level, and occasionally rises briefly above the "MV Threshold 1" level, indicating an increase in patient activity and an impending transition from the "sleep" state to the "awake" state. Subsequent to the time labeled "Patient Wakes Up" in FIG. 7, the "MV Stdev Long" value remains above the "MV Threshold 1" and "MV Threshold 2" levels, indicating a relatively high level of patient activity characteristic of the "awake" state of the patient.

Figure 8:
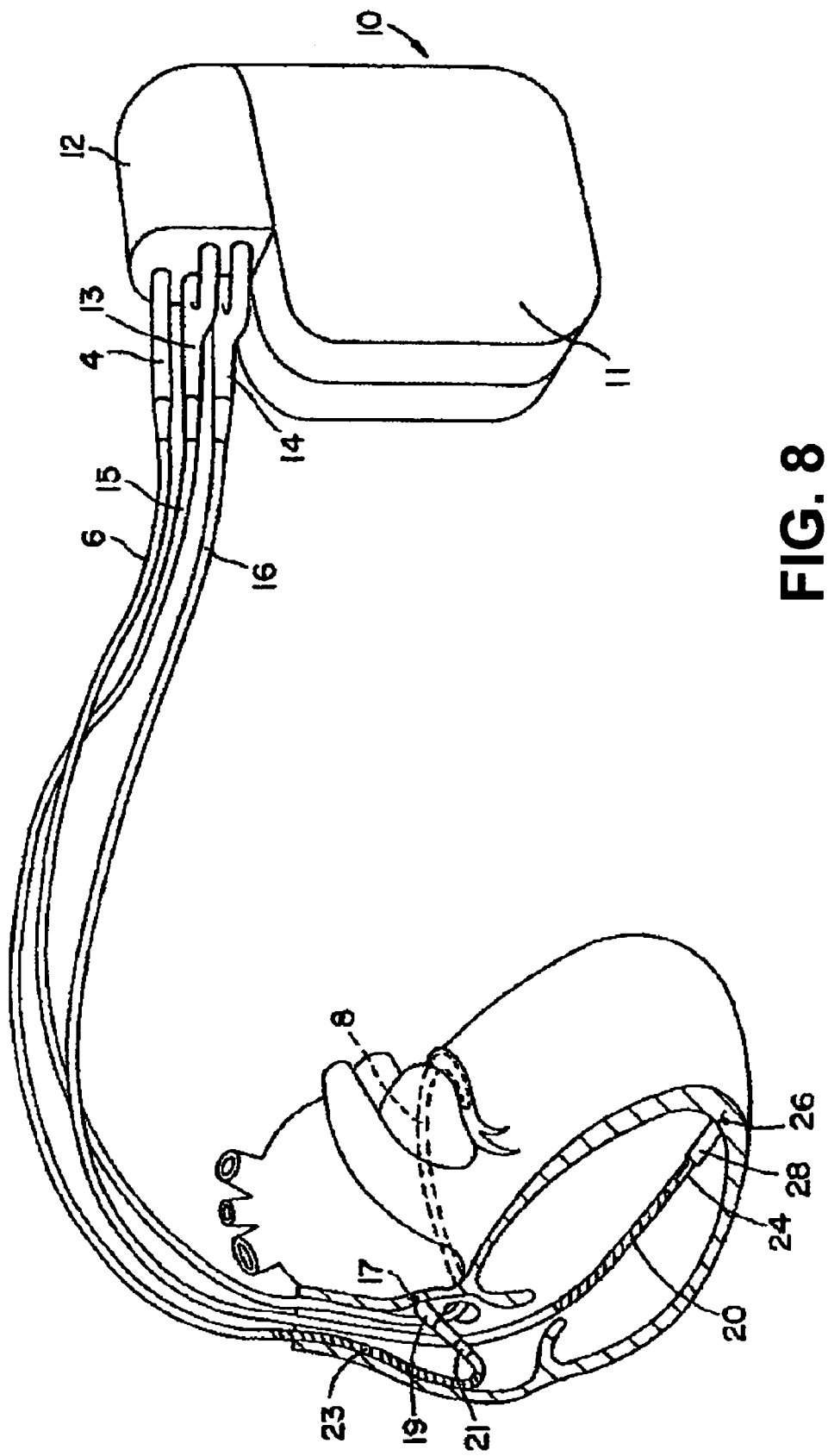
FIG. 8 is an illustration of an alternative embodiment of an implantable medical device system including an implantable cardioverter defibrillator.

FIG. 8 is an illustration of an alternative embodiment of an implantable medical device system including an implantable cardioverter defibrillator, referred to hereafter as "ICD", 10 coupled to a patient's heart by way of three leads 6, 15, and 16. A connector block 12 receives the proximal end of a right ventricular lead 16, a right atrial lead 15 and a coronary sinus lead 6, used for positioning electrodes for sensing and stimulation in three or four heart chambers. In FIG. 8, the right ventricular lead 16 is positioned such that its distal end is in the right ventricle (RV) for sensing right ventricular cardiac signals and delivering pacing or shocking pulses in the right ventricle. For these purposes, right ventricular lead 16 is equipped with a ring electrode 24, a tip electrode 26, optionally mounted retractably within an electrode head 28, and RV coil electrode 20, each of which are connected to an insulated conductor contained within the body of lead 16. The proximal end of the insulated conductors are coupled to corresponding connectors carried by a connector 14 at the proximal end of lead 16 for providing electrical connection to the ICD 10.

The right atrial lead 15 is positioned such that its distal end is in the vicinity of the right atrium and the superior vena cava (SVC). Lead 15 is equipped with a ring electrode 21 and a tip electrode 17, optionally mounted retractably within electrode head 19, for sensing and pacing in the right atrium. Lead 15 is further equipped with an SVC coil electrode 23 for delivering high-energy shock therapy. The ring electrode 21, the helix electrode 17 and the SVC coil electrode 23 are each connected to an insulated conductor with the body of the right atrial lead 15. Each insulated conductor is coupled at its proximal end to a connector terminal carried by connector 13.

The coronary sinus lead 6 is advanced within the vasculature of the left side of the heart via the coronary sinus and great cardiac vein. The coronary sinus lead 6 is shown in the embodiment of FIG. 8 as having a defibrillation coil electrode 8 that may be used in combination with either the RV coil electrode 20 or the SVC coil electrode 23 for delivering electrical shocks for cardioversion and defibrillation therapies. In other embodiments, coronary sinus lead 6 may also be equipped with a distal tip electrode and ring electrode for pacing and sensing functions in the left chambers of the heart. The coil electrode 8 is coupled to an insulated conductor within the body of lead 6, which provides connection to the proximal connector 4.

For sensing and pacing functions, the electrodes 17 and 21 or 24 and 26 may be used as bipolar pairs, commonly referred to as a "tip-to-ring" configuration, or individually in a unipolar configuration with the device housing 11 serving as the indifferent electrode, commonly referred to as the "can" or "case" electrode. The device housing 11 may also serve as a subcutaneous defibrillation electrode in combination with one or more of the defibrillation coil electrodes 8, 20 or 23 for defibrillation of the atria or ventricles.

It is recognized that alternate lead systems may be substituted for the three lead system illustrated in FIG. 8. While a particular multi-chamber ICD and lead system is illustrated in FIG. 8, methodologies included in the present invention may be adapted for use with a single chamber atrial cardioverter/defibrillator, dual chamber ICDs, or other multichamber ICDs.

Figure 9:
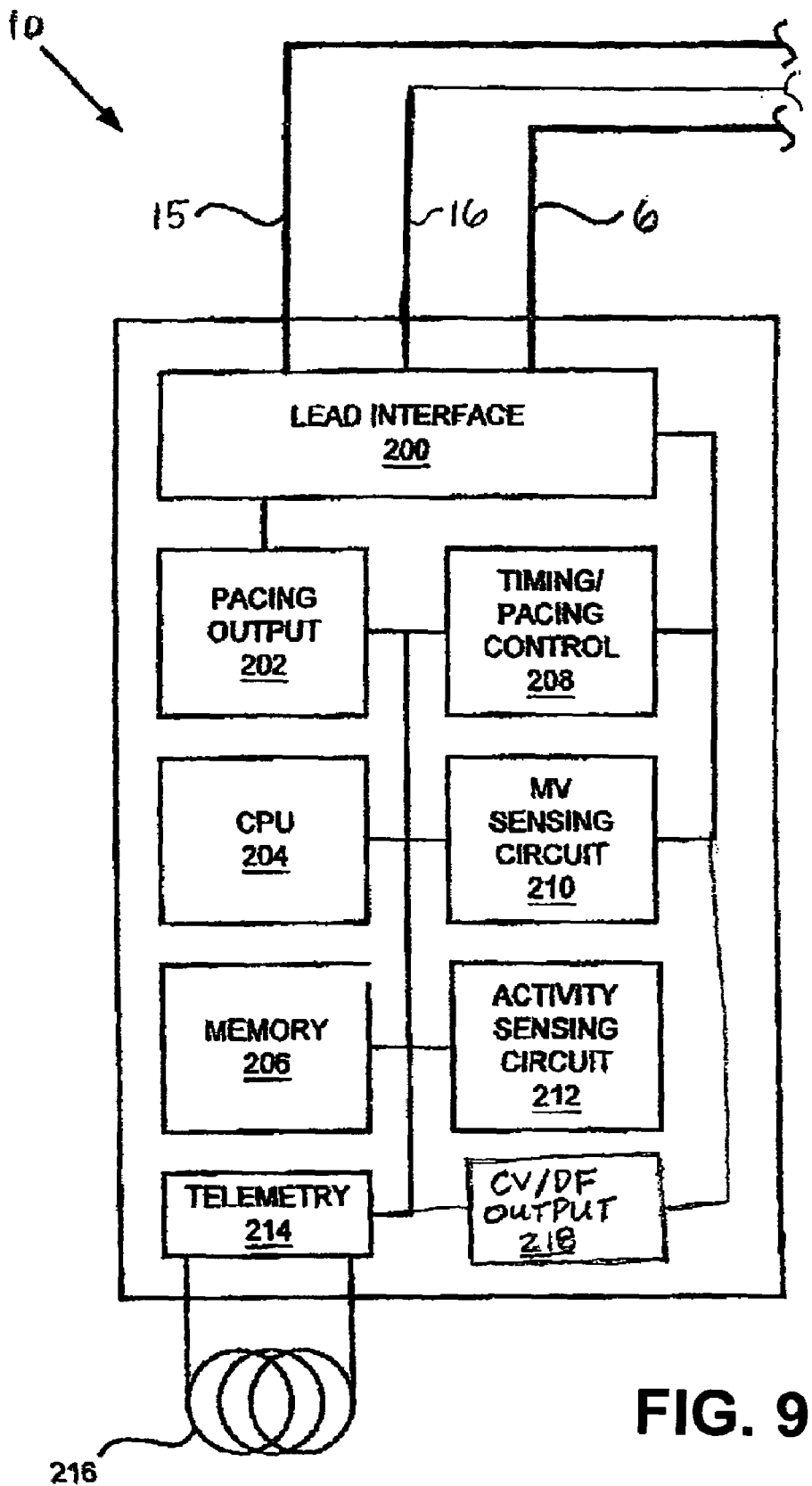
FIG. 9 is a diagram of one embodiment of the ICD of FIG. 8.

FIG. 9 is a diagram of one embodiment of the ICD of FIG. 8. ICD 10 produces high-energy shock pulses delivered to the heart via coil electrodes 20, 23 and/or 8 in response to detecting fibrillation. In the embodiment of FIG. 9, the ICD 10 includes lead interface circuitry 200, pacing output circuitry 202, a central processing unit (CPU) 204, a memory 206, timing/pacing control circuitry 208, a MV sensing circuit 210, an activity sensing circuitry 212, a telemetry unit 214, and an antenna 216, all of which may correspond generally to the identically-labeled components included in pacemaker 102 described above in conjunction with FIG. 9. ICD 10 additionally includes cardioversion/defibrillation output unit 218 for delivering high-voltage shock pulses.

The lead interface circuitry 200 is adapted for receiving the high-voltage right atrial lead 15, high-voltage right ventricular lead 16, and high-voltage coronary sinus lead 6. The electrodes carried by the leads 15, 16, and 6 may be selected via lead interface circuitry 200 for the various sensing, pacing, and cardioversion/defibrillation functions of ICD 10.

The timing/pacing control circuitry 208 includes sensing circuitry that receives and detects intrinsic electrical signals from sensing electrodes included on right atrial lead 15 and right ventricular lead 16. Timing/pacing control circuitry 208 includes various registers for storing values indicative of programmed parameters of the ICD 10, and various counters for performing timing functions. For example, the durations of escape intervals used in controlling the timing of pacing pulses delivered by ICD 10 are stored by timing/pacing control circuitry 208. The value of a count present in an escape interval counter when reset by sensed R-waves or P-waves can be used to measure R-R intervals, P-P intervals, P-R intervals, and R-P intervals, which measures are stored in memory 206 and used to diagnose the occurrence of a variety of arrhythmias by CPU 204.

Timing/pacing and control 208 may further include an analog-to-digital converter to digitize electrical signals received from the heart from sensing electrodes on leads 15 and 16. CPU 204 may employ digital signal analysis techniques to characterize the digitized signals received from timing pacing/control 208 and stored in memory 206 to recognize and classify the patient's heart rhythm employing any of the numerous signal processing methods known in the art.

In response to the detection of atrial or ventricular tachycardia, an anti-tachycardia pacing therapy may be delivered to the patient's heart by loading a regimen from CPU 204 into the pacer timing/control circuitry 208 according to the type of tachycardia detected. In the event that higher voltage cardioversion or defibrillation shock pulses are required, CPU 204 activates the cardioversion/defibrillation output unit 218 to initiate charging of high voltage capacitors via a charging circuit included therein. Timing of the delivery of the defibrillation or cardioversion shock pulse is controlled by pacer timing/control circuitry 208.

In accordance with the present invention, activation of cardioversion/defibrillation output unit 218 by CPU 204 may be delayed or cancelled pending the detection of sleep according to minute ventilation values provided by MV sensing circuit 210 to CPU 204 as described above. In modern ICDs, the particular arrhythmia therapies are programmed into the device ahead of time by the physician, and a menu of therapies is typically provided. The menu of therapies is often referred to as "tiered" therapies in that the therapies tend to progress from relatively lower-energy, less aggressive therapies, to higher-energy, more aggressive therapies. For example, on initial detection of tachycardia, an anti-tachycardia pacing therapy may be selected. On redetection of tachycardia, a more aggressive anti-tachycardia pacing therapy may be scheduled. If repeated attempts at anti-tachycardia pacing therapies fail, a higher-level cardioversion shock pulse therapy may be selected thereafter. The amplitude of a cardioversion/defibrillation shock may be incremented in response to failure of an initial shock or shocks to terminate tachycardia/fibrillation.

When such menus of therapies are available, a tiered therapy sequence may be initiated by CPU 204 in response to a detected atrial arrhythmia. On redetection, the therapy sequence may proceed up to a programmed high-voltage shock therapy. A programmed shock therapy may be postponed until a predetermined time after sleep onset is detected by CPU 204 according to the method 300 of FIGS. 3A through 3D.

Alternatively, when atrial arrhythmias requiring a high-voltage shock therapy are detected simultaneously with the detection of a sustained sleep detection, the programmed shock therapy may be delivered without delay. However, if an atrial arrhythmia requiring a high-voltage shock therapy is detected without concurrent sleep detection by CPU 204, any programmed high-voltage shock therapies may be canceled. Programmed pacing therapies or lower-voltage cardioversion therapies may proceed according to a menu of therapies.

Figure 10:
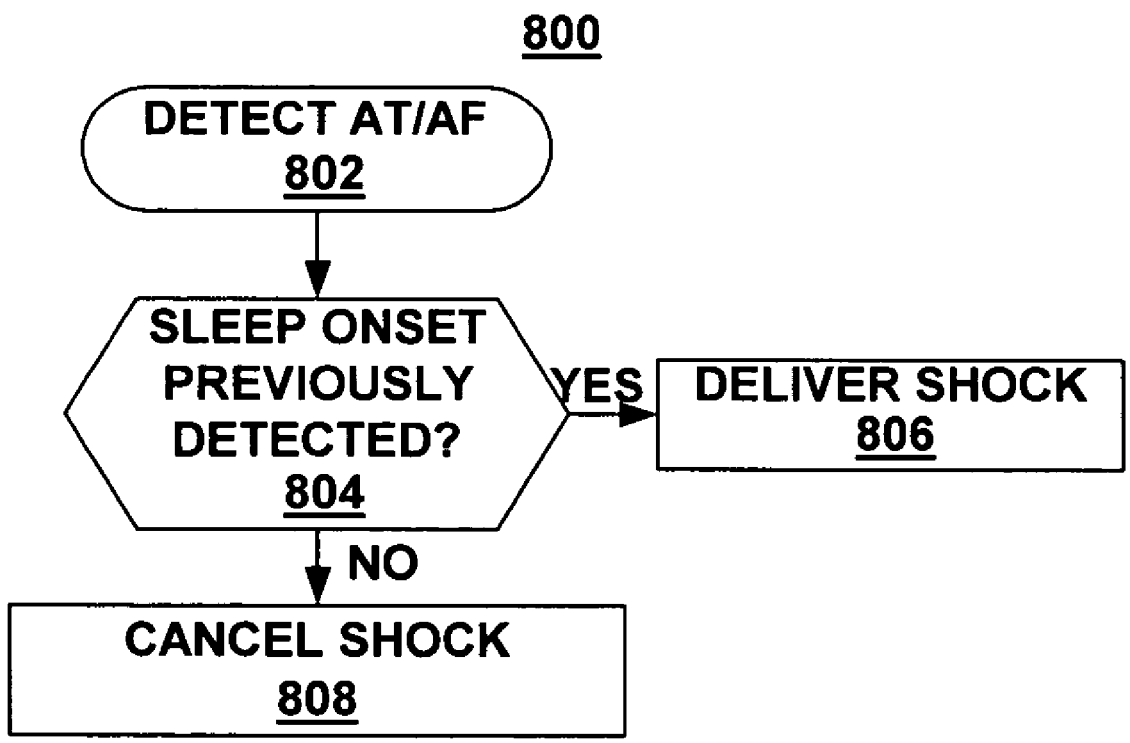
FIG. 10 is a flow chart summarizing the steps performed in one embodiment of a method for controlling the delivery of high-energy shock pulses for treating atrial arrhythmias pending the detection of sleep.

FIG. 10 is a flow chart summarizing the steps performed in one embodiment of a method for controlling the delivery of high-energy shock pulses for treating atrial arrhythmias pending the detection of sleep. Method 800 is initiated at step 802 upon detection of AT or AF. At step 804, a determination is made whether sleep onset was detected within a predetermined interval of time prior to the AT/AF detection. Sleep onset is preferably detected based on the deviation of MV values from a MV statistical parameter as described previously in conjunction with FIGS. 3A through 3D. However, sleep onset may also be detected using other known detection schemes, such as described, for example, in U.S. Pat. No. 6,128,534 issued to Park et al., U.S. Pat. No. 5,814,087 issued to Renrie, and U.S. Pat. No. 5,476,483 issued to Bornzin et al., all of which are incorporated herein by reference in their entireties.

If sleep onset was previously detected within the predetermined time interval such that the patient is currently believed to be asleep, a programmed cardioversion/defibrillation (CV/DF) shock is delivered at step 806. If sleep onset was not previously detected within a predetermined time interval, as determined at decision step 804, a programmed CV/DF shock is cancelled at step 808. It is to be understood that other arrhythmia therapies programmed to be delivered in a menu of therapies may be delivered upon detection of AT/AF at step 802. If a high-energy cardioversion or defibrillation shock is included in the menu of therapies, however, prior to preparing for shock delivery, i.e., prior to initiating capacitor charging, a verification that sleep onset was previously detected is made (step 804). The sleep onset detection is preferably made within a predetermined window of time, for example within the last 15 to 30 minutes, such that the patient is still expected to be asleep.

Figure 11:
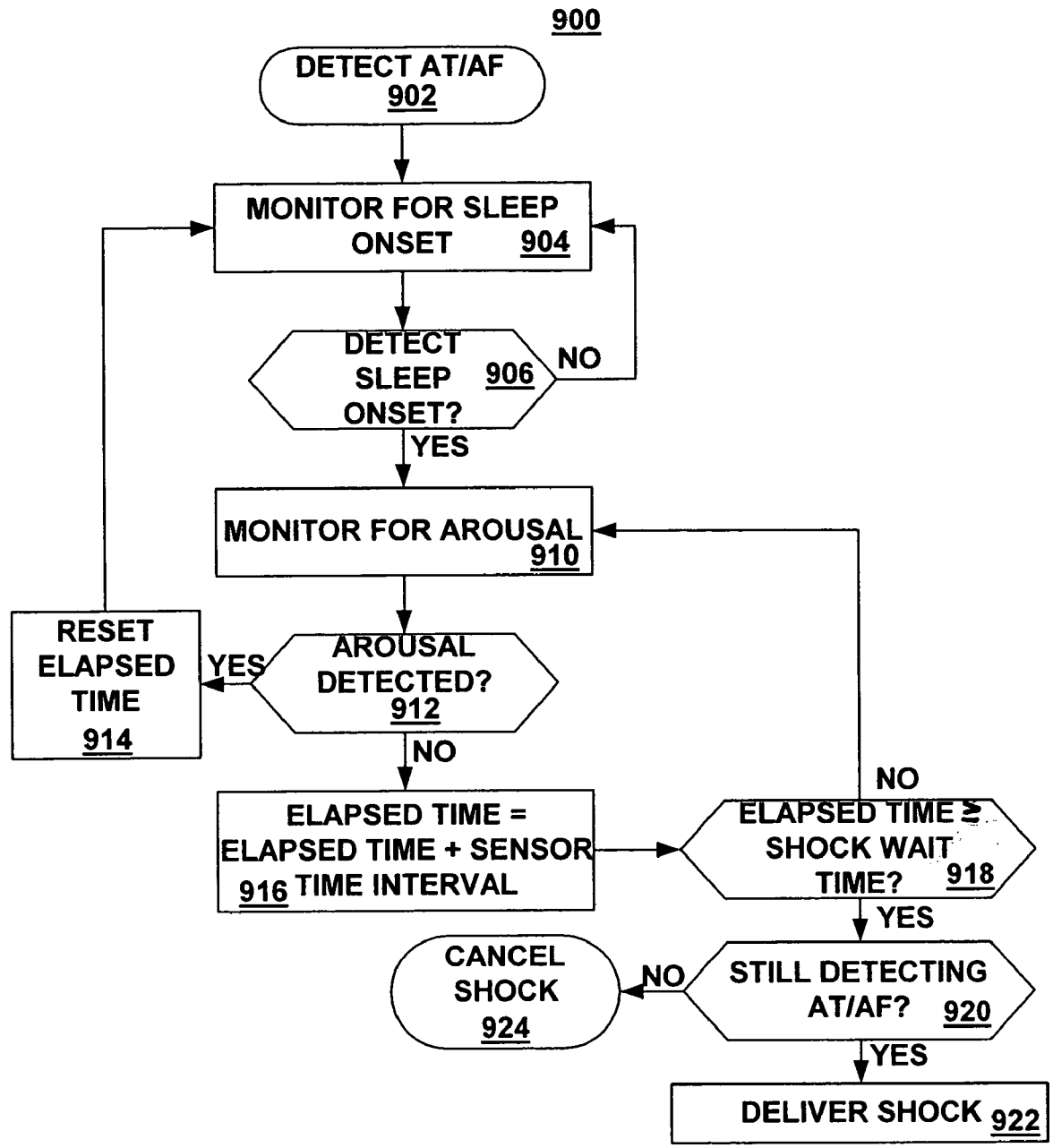
FIG. 11 is a flow chart summarizing the steps performed in an alternative embodiment of a method for controlling the delivery of high-energy shock pulses for treating atrial arrhythmias pending the detection of sleep.

FIG. 11 is a flow chart summarizing the steps performed in an alternative embodiment of a method for controlling the delivery of high-energy shock pulses for treating atrial arrhythmias pending the detection of sleep. Rather than canceling a programmed shock therapy if sleep onset has not been detected, a programmed shock therapy may be delayed until a time after sleep onset is detected. Method 900 begins at step 902 upon AT/AF detection, after which monitoring for the onset of sleep is performed at step 904. Sleep onset is detected based on long-term and relatively shorter-term MV parameter evaluation as described previously.

If sleep onset is detected, as determined at decision step 906, method 900 proceeds to step 910 to monitor for arousal. Otherwise, method 900 continues monitoring for sleep onset by returning to step 904. At step 904, MV parameter values are determined at the end of each MV sensor time interval, e.g., at the end of 2 seconds. At step 906, a comparative analysis of the MV parameter values, e.g., "MV Stdev Long" and "MV Stdev Short" as described previously, for determining if the onset of sleep has occurred.

Monitoring for arousal at step 910 involves a similar process in that at the end of each MV sensor time interval, MV parameter values are determined. These MV parameter values are evaluated in a comparative analysis at step 912 to determine if sleep is no longer indicated, i.e., arousal has occurred. As described previously, while the patient is sleeping, the "MV Stdev Long" value is typically greater than or equal to the "MV Stdev Short" value. However, when the patient wakes up abruptly and becomes active, the "MV Stdev Short" value will become greater than the "MV Stdev Long" value, indicating the patient has transitioned from the "sleep" state to the "awake" state. Thus, arousal may be detected at step 912 based on a "MV Stdev Short value" becoming greater than the "MV Stdev Long" value subsequent to the sleep onset detection.

If arousal is detected, method 900 returns to step 904 to resume monitoring for sleep onset. Any elapsed time measured since the onset of sleep detection is reset to zero at step 914. If arousal is not detected at decision step 912, the elapsed time since sleep onset detection is measured at step 916. The MV sensor time interval, e.g., 2 seconds, is added to the "current" elapsed time value at step 916.

At step 918, the elapsed time is compared to a "shock wait time." The "shock wait time" is a predetermined, programmable amount of time after which a delayed CV/DF shock will be delivered. The "shock wait time" preferably corresponds to the time normally required for a patient to reach a deep sleep stage after sleep onset. Typically, a person enters deep sleep approximately 20 minutes after sleep onset occurs if not aroused or disturbed. A "shock wait time" may appropriately be set, therefore, between 20 and 60 minutes, for example.

If the elapsed time has reached the "shock wait time" as determined at decision step 918, the ICD 10 may verify that the AT/AF is still being detected at decision step 920 and, if so, deliver the delayed CV/DF shock thereafter at step 922. If the elapsed time since sleep onset detection has not reached the "shock wait time," the patient is presumably not yet in a deep sleep stage. Method 900 returns to step 910 to continue monitoring for arousal and measuring the elapsed time since sleep onset if arousal is not detected.

If AT/AF is no longer being detected after the elapsed time equals the "shock wait time", as determined at decision step 918, delivery of the delayed shock is no longer appropriate. Method 900 is then terminated at step 924, and the delayed shock is canceled.

Figure 12:
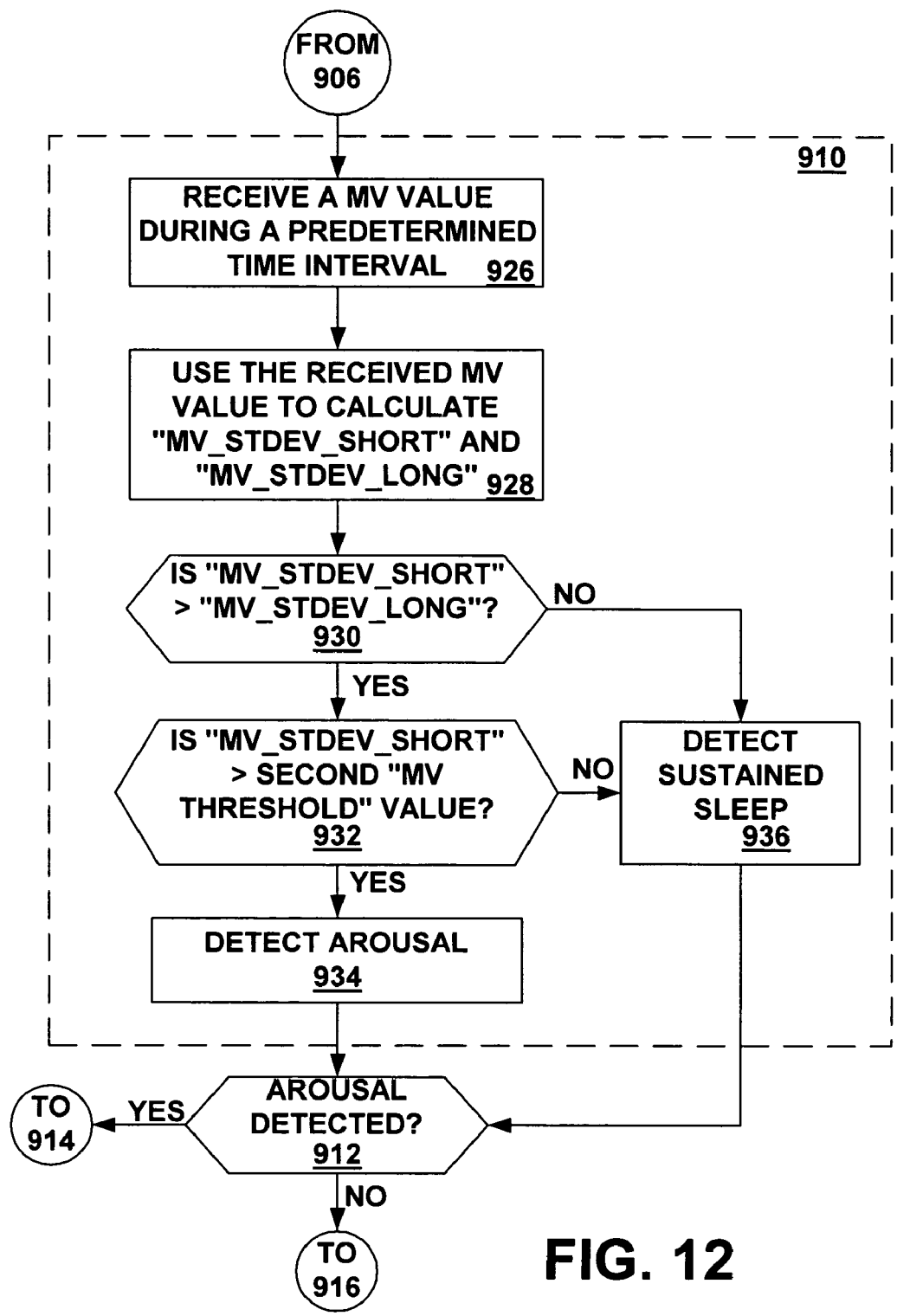
FIG. 12 is a flow chart providing additional details included in one embodiment of a step for detecting arousal included in the method of FIG. 11.

FIG. 12 is a flow chart providing additional details included in one embodiment of the step for detecting arousal included in method 900 of FIG. 11. Steps for monitoring for arousal that may be included in step 910 of method 900 are grouped within dashed line in FIG. 12. After detecting sleep onset at step 906 of method 900 (FIG. 11) as described previously, monitoring for arousal commences at step 926 wherein computational circuitry receives the next MV value determined during a predetermined time interval, e.g., 2 seconds, from MV sensing circuitry. The received MV value is used to calculate a current "MV Stdev Short" value and a current "MV Stdev Long" value as indicated at step 928 and as described previously. At decision step 930, the current "MV Stdev Short" value is compared to the current "MV Stdev Long" value. If the "MV Stdev Short" value has become greater than the "MV Stdev Long" value, the patient may have become active indicating arousal.

If the current "MV Stdev Short" value has also exceeded the second "MV threshold" value described previously, arousal is detected at step 934. On the other hand, if the "MV Stdev Short" value is not greater than the "MV Stdev Long" value (step 930), or if the "MV Stdev Short" value is greater than the "MV Stdev Long" value but is still less than the second "MV Threshold" value (step 932), a "sleep" state detection is sustained as indicated at step 936. After completing the subroutine represented by steps 926 through 936, method 900 proceeds to decision step 912 and thereafter to step 914 or 916 (FIG. 11) depending on whether arousal has been detected.

Figure 13:
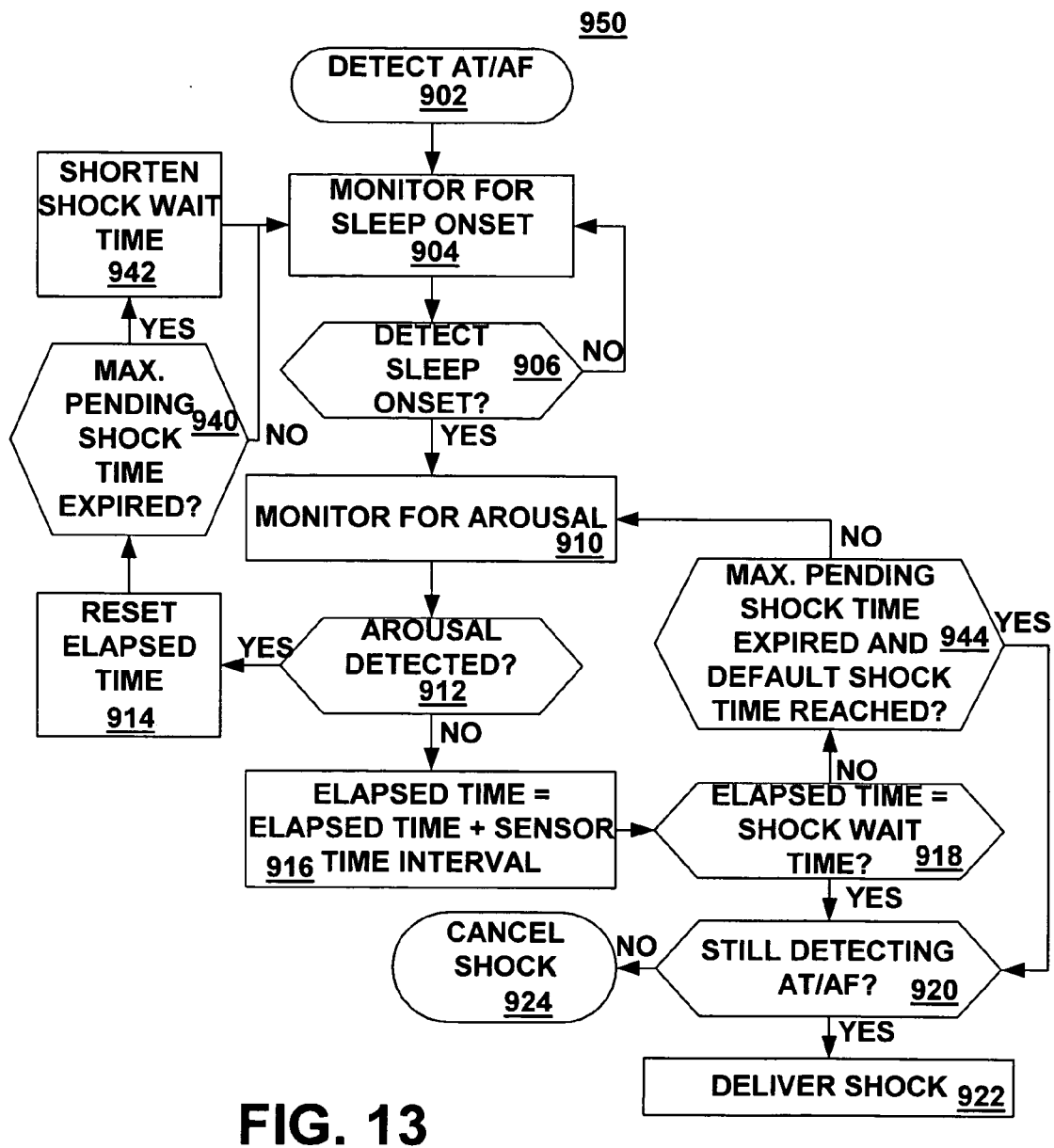
FIG. 13 is a flow chart summarizing the steps performed in yet another embodiment of a method for controlling the delivery of high-energy shock pulses for treating atrial arrhythmias pending the detection of sleep.

FIG. 13 is a flow chart summarizing the steps performed in yet another embodiment of a method for controlling the delivery of high-energy shock pulses for treating atrial arrhythmias pending the detection of sleep. Steps 902 through 924 included in method 950 shown in FIG. 13 correspond to identically-labeled steps included in method 900 of FIG. 11, described above. During execution of the previously-described method 900, a pending shock therapy may be withheld indefinitely if the programmed "shock wait time" is never reached (at step 918) after a sleep onset detection is made (step 906). The "shock wait time" may not be reached during a period of sleep, for example, when a patient is restless or experiences frequent arousals during the night. Thus, a pending shock therapy will not be delivered. It may be undesirable, however, to withhold a pending AT/AF shock therapy for an extended period of time, for example for more than 24 to 48 hours. In such cases, a pending shock therapy may be scheduled to occur at a particular time of day, e.g., 4 a.m., or after a shortened "shock wait time," whichever occurs first.

Thus, method 950 of FIG. 13 includes additional steps for ensuring that a pending shock therapy is not withheld indefinitely. If arousal is detected at step 912 of FIG. 13, after a sleep onset detection is made at step 906, an elapsed time counter is reset at step 914 as described previously. However, before returning to step 904 to monitor for sleep onset again, method 950 determines if a "maximum pending shock time" has expired at step 940. If not, method 950 proceeds to step 904. However, if a "maximum pending shock time" has expired, the "shock wait time" is shortened at step 942. By shortening the "shock wait time," the pending shock therapy is more likely to be delivered following the next sleep onset detection.

A "maximum pending shock time" may be defined as an interval of time measured from the time of AT/AF detection. A maximum pending shock time may be programmed as a number of minutes or hours following an AT/AF detection, e.g., 12, 18 or 24 hours. Alternatively, a "maximum pending shock time" may be programmed to correspond to a time of day. For example, the maximum pending shock time may expire at a scheduled time of day, such as 7:00 a.m., indicating the end of "night time." If the "shock wait time" is not reached during the first night following AT/AF detection, the "maximum pending shock time" will be reached. Upon reaching the "maximum pending shock time," at step 940 the "shock wait time" is shortened at step 942.

After the "shock wait time" is shortened, method 950 continues to step 904 to monitor for the onset of sleep. If the elapsed time measured following a sleep detection (step 916) reaches the shortened "shock wait time" (step 918), and AT/AF is still being detected (step 920), the shock therapy is delivered at step 922. However, if the shortened "shock wait time" is not reached (step 918), and the "maximum pending shock time" has been exceeded, a shock therapy may be delivered at a scheduled, "default" shock delivery time. Thus, if the elapsed time does not reach the shortened "shock wait time" at decision step 918, method 950 determines if the "maximum pending shock time" has been exceeded and a scheduled "default" shock delivery time has been reached at decision step 944. If these conditions are satisfied, the shock therapy is delivered at step 922 after verifying the sustained AT/AF detection at step 920. A "default" shock delivery time may be programmed to a time of day, for example 4:00 a.m., at which the patient is expected to be resting.

If the scheduled "default" shock time has not been reached at decision step 944, method 950 returns to step 910 to continue to monitor for arousal. The pending shock therapy will thus be delivered, at step 922: after the originally programmed "shock wait time" following a sleep onset detection; after a shortened "shock wait time" if a "maximum pending shock time" has expired; or at a scheduled "default" shock delivery time if a "maximum pending shock time" has expired, which ever occurs first.

Some of the techniques described above may be embodied as a computer-readable medium comprising instructions for a programmable processor such as microprocessor 204 or timing/control circuitry 208 shown in FIGS. 2 and 9. The programmable processor may include one or more individual processors, which may act independently or in concert. A "computer-readable medium" includes but is not limited to any type of computer memory such as floppy disks, conventional hard disks, CR-ROMS, Flash ROMS, nonvolatile ROMS, RAM and a magnetic or optical storage medium. The medium may include instructions for causing a processor to perform any of the features described above for initiating a session of the escape rate variation according to the present invention.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. An implantable medical device capable of being implanted in a patient, comprising:
   a therapy component configured to provide a therapy to the patient;
   sensing circuitry sensing a physiologic parameter corresponding to minute ventilation values indicative of a minute ventilation of the patient; and
   a microprocessor coupled to the therapy component and the sensing circuitry to detect onset of a first state of the patient in response to the sensed physiologic parameter, and to determine whether the onset of the first state is detected for a first predetermined time period, wherein the first state corresponds to an asleep state, and
   wherein the microprocessor receives a plurality of the minute ventilation values at predetermined time intervals over a period of time to generate a first distribution rate of minute ventilation values of the plurality of minute ventilation values received during first time intervals m of the predetermined time intervals, including a current time interval and first preceding time intervals m-1, and a second distribution rate of minute ventilation values received during second time intervals n of the predetermined time intervals, including the current time interval and second preceding time intervals n1, wherein the onset of the first state is detected in response to the second distribution rate being greater than the first distribution rate.

2. The device of claim 1, wherein delivery of the therapy is cancelled in response to the onset of the first state not being detected for the predetermined time period.

3. The device of claim 1, wherein the therapy component senses intrinsic signals of the patient and the microprocessor detects a predetermined event in response to the sensed intrinsic signals.

4. The device of claim 3, wherein the first predetermined time period corresponds to a period of time prior to detection of the predetermined event.

5. The device of claim 4, wherein the period of time is between approximately 15 and 30 minutes.

6. The device of claim 1, wherein the first predetermined time period corresponds to a period of time since the detected onset of the first state.

7. The device of claim 6, wherein the period of time is between approximately 20 and 60 minutes.

8. The device of claim 6, wherein the therapy component senses intrinsic signals of the patient and the microprocessor detects a predetermined event in response to the sensed intrinsic signals and determines whether the predetermined event is detected subsequent to the onset of the first state being detected for the first predetermined time period.

9. The device of claim 1, wherein the microprocessor generates a threshold corresponding to a transition of the patient between the first state and a second state in response to the minute ventilation values, determines the first state is sustained in response to one of the first distribution rate not being greater than the second distribution rate, and the first distribution rate being greater than the second distribution rate and not being greater than the threshold, and determines, in response to the first state being sustained, an elapsed time since the detected onset of the first state, wherein the onset of the first state is determined to be detected for the first predetermined time period in response to the elapsed time being greater than or equal to the first predetermined time period.

10. The device of claim 9, wherein the therapy component senses intrinsic signals of the patient, and wherein the microprocessor detects a predetermined event in response to the sensed intrinsic signals, and determines whether the predetermined event is detected subsequent to the onset of the first state being detected for the first predetermined time period.

11. The device of claim 9, wherein the microprocessor determines, in response to the first state not being sustained, whether a second predetermined time period has expired, and reduces the first predetermined time period in response to the second predetermined time period being expired.

12. The device of claim 11, wherein the therapy component senses intrinsic signals of the patient and wherein the microprocessor determines, in response to the first state being sustained and the elapsed time subsequently not being greater than or equal to the first predetermined time period, whether a predetermined delivery time has been reached and the second predetermined time period has expired, detects a predetermined event in response to the sensed intrinsic signals, determines, in response to the predetermined delivery time being reached and the second predetermined time period having expired, whether the predetermined event is detected, and delivers the therapy in response to the predetermined event being detected.

13. The device of claim 1, wherein the microprocessor generates a first threshold and a second threshold corresponding to a transition of the patient between the first state and a second state corresponding to an awake state in response to the minute ventilation values, detects onset of the first state in response to the second distribution rate being less than the first threshold and the second distribution rate being greater than or equal to the first distribution rate, and detects a transition between the first state and the second state in response to the second distribution rate being less than the first distribution rate and the first distribution rate being greater than the second threshold.

14. A method of providing therapy to a patient having an implantable medical device, comprising:
    sensing a physiologic parameter corresponding to minute ventilation values indicative of a minute ventilation of the patient;
    detecting onset of a first state of the patient in response to the sensed parameter, wherein the first state corresponds to an asleep state; and
    determining whether the onset of the first state is detected for a first predetermined time period,
    wherein detecting the onset of the first state comprises:
        determining a plurality of the minute ventilation values at predetermined time intervals over a period of time;
        generating a first distribution rate of minute ventilation values of the plurality of minute ventilation values received during first time intervals m of the predetermined time intervals, including a current time interval and first preceding time intervals m1, and a second distribution rate of minute ventilation values received during second time intervals n of the predetermined time intervals, including the current time interval and second preceding time intervals n1; and
        detecting the onset of the first state in response to the second distribution rate being greater than the first distribution rate.

15. The method of claim 14, further comprising canceling the therapy in response to the onset of the first state not being detected for the first predetermined time period.

16. The method of claim 14, further comprising sensing intrinsic signals of the patient and detecting a predetermined event in response to the sensed intrinsic signals, wherein the first predetermined time period corresponds to a period of time prior to detection of the predetermined event.

17. The method of claim 16, wherein the period of time is between approximately 15 and 30 minutes.

18. The method of claim 14, wherein the first predetermined time period corresponds to a period of time since the detected onset of the first state.

19. The method of claim 18, wherein the period of time is between approximately 20 and 60 minutes.

20. The method of claim 18, further comprising:
    sensing intrinsic signals of the patient and detecting a predetermined event in response to the sensed intrinsic signals; and
    determining whether the predetermined event is detected subsequent to the onset of the first state being detected for the first predetermined time period.

21. The method of claim 14, further comprising:
    generating a threshold corresponding to a transition of the patient between the first state and a second state in response to the minute ventilation values;
    determining whether the first state is sustained, the first state being determined to be sustained in response to one of the first distribution rate not being greater than the second distribution rate, and the first distribution rate being greater than the second distribution rate and not being greater than the threshold; and
    determining, in response to the first state being sustained, an elapsed time since the detected onset of the first state, wherein determining whether the onset of the first state is detected for a first predetermined time period comprises determining whether the elapsed time is greater than or equal to the first predetermined time period.

22. The method of claim 21, further comprising:
    sensing intrinsic signals of the patient and detecting a predetermined event in response to the sensed intrinsic signals; and
    determining whether the predetermined event is detected subsequent to the onset of the first state being detected for the first predetermined time period.

23. The method of claim 14, further comprising
    generating a first threshold and a second threshold corresponding to a transition of the patient between the first state and a second state in response to the minute ventilation values; and
    detecting onset of the first state in response to the second distribution rate being less than the first threshold and the second distribution rate being greater than or equal to the first distribution rate, and detecting a transition between the first state and the second state in response to the second distribution rate being less than the first distribution rate and the first distribution rate being greater than the second threshold.

24. The method of claim 21, further comprising:
    determining, in response to the first state not being sustained, whether a second predetermined time period has expired; and
    reducing the first predetermined time period in response to the second predetermined time period being expired.

25. The method of claim 24, further comprising:
    determining, in response to the first state being sustained and the elapsed time subsequently not being greater than or equal to the first predetermined time period, whether a predetermined delivery time has been reached and the second predetermined time period has expired;
    sensing intrinsic signals of the patient and detecting a predetermined event in response to the sensed intrinsic signals;
    determining, in response to the predetermined delivery time being reached and the second predetermined time period having expired, whether the predetermined event is detected; and
    delivering the therapy in response to the predetermined event being detected.

26. An implantable medical device capable of being implanted in a patient, comprising:
    means for sensing a physiologic parameter corresponding to minute ventilation values of a minute ventilation of the patient;
    means for detecting onset of a first state of the patient in response to the sensed parameter, wherein the first state corresponds to an asleep state; and
    means for determining whether the onset of the first state is detected for a first predetermined time period,
    wherein means for detecting the onset of the first state comprises:

means for determining a plurality of the minute ventilation values at predetermined time intervals over a period of time:
means for generating a first distribution rate of minute ventilation values of the plurality of minute ventilation values received during first time intervals m of the predetermined time intervals, including a current time interval and first preceding time intervals m1, and a second distribution rate of minute ventilation values received during second time intervals n of the predetermined time intervals, including the current time interval and second preceding time intervals n1; and
means for detecting the onset of the first state in response to the second distribution rate being greater than the first distribution rate.

27. The device of claim 26, further comprising means for canceling the therapy in response to the onset of the first state not being detected for the first predetermined time period.

28. The device of claim 26, further comprising:
means for sensing intrinsic signals of the patient; and
means for detecting a predetermined event in response to the sensed intrinsic signals, wherein the predetermined time period corresponds to a period of time prior to detection of the predetermined event.

29. The device of claim 28, wherein the period of time is between approximately 15 and 30 minutes.

30. The device of claim 26, wherein the first predetermined time period corresponds to a period of time since the detected onset of the first state.

31. The device of claim 30, wherein the period of time is between approximately 20 and 60 minutes.

32. The device of claim 30, further comprising:
means for sensing intrinsic signals of the patient;
means for detecting a predetermined event in response to the sensed intrinsic signals; and
means for determining whether the predetermined event is detected subsequent to the onset of the first state being detected for the first predetermined time period.

33. The device of claim 26, further comprising:
means for generating a threshold corresponding to a transition of the patient between the first state and a second state in response to the minute ventilation values;
means for determining whether the first state is sustained, the first state being determined to be sustained in response to one of the first distribution rate not being greater than the second distribution rate, and the first distribution rate being greater than the second distribution rate and not being greater than the threshold; and
means for determining, in response to the first state being sustained, an elapsed time since the detected onset of the first state, wherein the means for determining whether the onset of the first state is detected for a first predetermined time period comprises determining whether the elapsed time is greater than or equal to the first predetermined time period.

34. The device of claim 33, further comprising:
means for sensing intrinsic signals of the patient;
means for detecting a predetermined event in response to the sensed intrinsic signals; and
means for determining whether the predetermined event is detected subsequent to the onset of the first state being detected for the first predetermined time period.

35. The device of claim 26, further comprising
means for generating a first threshold and a second threshold corresponding to a transition of the patient between the first state and a second state in response to the minute ventilation values; and
means for detecting onset of the first state in response to the second distribution rate being less than the first threshold and the second distribution rate being greater than or equal to the first distribution rate, and
means for detecting a transition between the first state and the second state in response to the second distribution rate being less than the first distribution rate and the first distribution rate being greater than the second threshold.

36. The device of claim 33, further comprising:
means for determining, in response to the first state not being sustained, whether a second predetermined time period has expired; and
means for reducing the first predetermined time period in response to the second predetermined time period being expired.

37. The device of claim 36, further comprising:
means for determining, in response to the first state being sustained and the elapsed time subsequently not being greater than or equal to the first predetermined time period, whether a predetermined delivery time has been reached and the second predetermined time period has expired;
means for sensing intrinsic signals of the patient;
means for detecting a predetermined event in response to the sensed intrinsic signals;
means for determining, in response to the predetermined delivery time being reached and the second predetermined time period having expired, whether the predetermined event is detected; and
means for delivering the therapy in response to the predetermined event being detected.

38. A computer readable medium having computer executable instructions for performing a method comprising:
sensing a physiologic parameter corresponding to minute ventilation values indicative of a minute ventilation of the patient;
detecting onset of a first state of the patient in response to the sensed parameter, wherein the first state corresponds to an asleep state; and
determining whether the onset of the first state is detected for a first predetermined time period,
wherein detecting the onset of the first state comprises:
determining a plurality of the minute ventilation values at predetermined time intervals over a period of time;
generating a first distribution rate of minute ventilation values of the plurality of minute ventilation values received during first time intervals m of the predetermined time intervals, including a current time interval and first preceding time intervals m1, and a second distribution rate of minute ventilation values received during second time intervals n of the predetermined time intervals, including the current time interval and second preceding time intervals n1, and
detecting the onset of the first state in response to the second distribution rate being greater than the first distribution rate.

39. A computer readable medium having computer executable instructions for performing a method comprising:

sensing minute ventilation values indicative of a minute ventilation of the patient;

generating a first threshold and a second threshold corresponding to a physiologic transition of the patient between a first state and a second state in response to the minute ventilation values;

generating a first distribution rate of a plurality of the sensed minute ventilation values received during first time intervals of predetermined time intervals including a first current time interval m and first preceding time intervals m 1 and a second distribution rate of a plurality of the sensed minute ventilation values received during second time intervals of the predetermined time intervals including a second time interval n and second preceding time intervals n1;

detecting onset of the second state in response to the second distribution rate being less than the first threshold, an abrupt transition between the first state and the second state, and the second distribution rate being greater than or equal to the first distribution rate; and modifying the therapy in response to the detected onset of the second state.

* * * * *

UNITED STATES PATENT AND TRADEMARK OFFICE
CERTIFICATE OF CORRECTION

PATENT NO. : 7,206,635 B2
APPLICATION NO. : 10/736370
DATED : April 17, 2007
INVENTOR(S) : Yong Kyun Cho et al.

It is certified that error appears in the above-identified patent and that said Letters Patent is hereby corrected as shown below:

Col. 24, line 3, delete "n1" and insert in place there of --n-1--.
Col. 25, line 32, delete "m1" and insert in place there of --m-1--.
Col. 25, line 36, delete "n1" and insert in place there of --n-1--.
Col. 27, line 8, delete "m1" and insert in place there of --m-1--.
Col. 27, line 12, delete "n1" and insert in place there of --n-1--.
Col. 28, line 57, delete "m1" and insert in place there of --m-1--.
Col. 28, line 61, delete "n1" and insert in place there of --n-1--.
Col. 29, line 11, delete "m1" and insert in place there of --m-1--.
Col. 30, line 3, delete "n1" and insert in place there of --n-1--.

Signed and Sealed this

Twenty-seventh Day of January, 2009

JOHN DOLL
*Acting Director of the United States Patent and Trademark Office*